(12) United States Patent
McLeary et al.

(10) Patent No.: US 9,387,095 B2
(45) Date of Patent: Jul. 12, 2016

(54) PROSTHETICS AND ORTHOTICS

(71) Applicant: Touch Bionics Limited, Livingston (GB)

(72) Inventors: Gordon McLeary, Lochwinnoch Strathyclyde (GB); Hugh Gill, Paisley Strathclyde (GB)

(73) Assignee: TOUCH BIONICS LIMITED, Livingston (GB)

( * ) Notice: Subject to any disclaimer, the term of this patent is extended or adjusted under 35 U.S.C. 154(b) by 0 days.

(21) Appl. No.: 14/416,737

(22) PCT Filed: Jul. 23, 2013

(86) PCT No.: PCT/GB2013/051961
§ 371 (c)(1),
(2) Date: Jan. 23, 2015

(87) PCT Pub. No.: WO2014/016581
PCT Pub. Date: Jan. 30, 2014

(65) Prior Publication Data
US 2015/0190245 A1    Jul. 9, 2015

(30) Foreign Application Priority Data

Jul. 23, 2012   (GB) .................................. 1213030.8

(51) Int. Cl.
*A61F 2/54* (2006.01)
*A61F 2/58* (2006.01)
(Continued)

(52) U.S. Cl.
CPC . *A61F 2/54* (2013.01); *A61F 2/586* (2013.01); *A61F 2/583* (2013.01); *A61F 5/0102* (2013.01);
(Continued)

(58) Field of Classification Search
CPC ............. A61F 2/54; A61F 2/586; A61F 2/68; A61F 2002/6827; A61F 2002/6836
See application file for complete search history.

(56) References Cited

U.S. PATENT DOCUMENTS 2,669,727 A   2/1954   Opuszenski
3,866,246 A   2/1975   Seamone et al.
(Continued)

FOREIGN PATENT DOCUMENTS

CN    1803413    7/2006
EP    0145504    6/1985
(Continued)

OTHER PUBLICATIONS

Connolly, "Prosthetic hands from Touch Bionics," Industrial Robot: An International Journal, 35(4):290-293, 2008.
(Continued)

*Primary Examiner* — Bruce E Snow
(74) *Attorney, Agent, or Firm* — K&L Gates LLP

(57) ABSTRACT

A prosthesis or an orthosis such as a hand prosthesis (10) comprises a moveable component (12). The moveable component (12) has a motor (14) operable to drive a worm gear (16). The hand prosthesis (10) also comprises a worm gear wheel 18 fixedly mounted on a support member (20). The moveable component (12) extends generally tangentially with respect to the worm gear wheel (18) and is mounted for rotation about the worm gear wheel (18). The worm gear (16) is in engagement with the worm gear wheel (18) such that, when the motor (14) is operated in use of the hand prosthesis (10), the moveable component (12) rotates about the worm gear wheel 18. The moveable component (12) includes two electrical contact members (50a) and (50b) and the worm gear wheel (18) includes two electrical contact surfaces (52a) and (52b). The electrical contact members (50a), (50b) and the electrical contact surfaces (52a), (52b) are arranged to slidably contact one another as the moveable component (12) rotates about the worm gear wheel (18).

34 Claims, 10 Drawing Sheets

(51) Int. Cl.
  *A61F 5/01* (2006.01)
  *A61F 2/68* (2006.01)
  *A61F 2/70* (2006.01)
  *A61F 2/76* (2006.01)

(52) U.S. Cl.
  CPC ..... *A61F 2002/543* (2013.01); *A61F 2002/546* (2013.01); *A61F 2002/6836* (2013.01); *A61F 2002/6863* (2013.01); *A61F 2002/701* (2013.01); *A61F 2002/7625* (2013.01)

(56) References Cited

U.S. PATENT DOCUMENTS

| | | |
|---|---|---|
| 4,558,704 A | 12/1985 | Petrofsky |
| 4,623,354 A | 11/1986 | Childress et al. |
| 4,808,187 A | 2/1989 | Patterson et al. |
| 4,955,918 A | 9/1990 | Lee |
| 4,990,162 A | 2/1991 | LeBlanc et al. |
| 5,413,611 A | 5/1995 | Haslam, II et al. |
| 5,888,246 A | 3/1999 | Gow |
| 6,344,062 B1 | 2/2002 | Abboudi et al. |
| 7,316,304 B2 * | 1/2008 | Heravi .................. B60K 23/08 180/248 |
| 7,370,896 B2 | 5/2008 | Anderson et al. |
| 7,922,773 B1 | 4/2011 | Kuiken |
| 8,662,552 B2 | 3/2014 | Torres-Jara |
| 2003/0036805 A1 | 2/2003 | Senior |
| 2004/0078091 A1 | 4/2004 | Elkins |
| 2005/0192677 A1 | 9/2005 | Ragnarsdottir et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2008/0146981 A1 | 6/2008 | Greenwald et al. |
| 2008/0262634 A1 | 10/2008 | Puchhammer |
| 2010/0016990 A1 | 1/2010 | Kurtz |
| 2010/0116078 A1 | 5/2010 | Kim |
| 2010/0274365 A1 | 10/2010 | Evans et al. |

FOREIGN PATENT DOCUMENTS

| | | |
|---|---|---|
| EP | 1043003 | 10/2000 |
| GB | 1585256 | 2/1981 |
| GB | 2444679 | 6/2008 |
| JP | 53-11456 | 2/1978 |
| WO | 95/24875 | 9/1995 |
| WO | 00/69375 | 11/2000 |
| WO | 03/017878 | 3/2003 |
| WO | 03/017880 | 3/2003 |
| WO | 2006/069264 | 6/2006 |
| WO | 2007/063266 | 6/2007 |
| WO | 2007/076764 | 7/2007 |
| WO | 2007/076765 | 7/2007 |
| WO | 2007/127973 | 11/2007 |
| WO | 2008/044207 | 4/2008 |
| WO | 2008/098059 | 8/2008 |
| WO | 2008/098072 | 8/2008 |
| WO | 2010/018358 | 2/2010 |
| WO | 2011/001136 | 1/2011 |
| WO | 2011/022569 | 2/2011 |
| WO | 2011/036473 | 3/2011 |
| WO | 2011107778 | 9/2011 |

OTHER PUBLICATIONS

STIX, "Phantom Touch: Imbuing a Prosthesis with Manual Dexterity," Scientific American, Oct. 1998, pp. 41 and 44.
Search Report for GB Application No. GB0916895.6 dated Mar. 17, 2010, 5 pages.
Search Report for GB Application No. GB0910920.8 dated Mar. 26, 2010, 3 pages.
PCT International Search Report for PCT International Application No. PCT/GB2012/052021, mail date Nov. 26, 2012, 5 pages.
PCT Written Opinion of the International Searching Authority for PCT International Application No. PCT/GB2012/052021, mail date May 3, 2013, 6 pages.
PCT International Search Report for PCT International Application No. PCT/GB2012/052111, mail date Nov. 26, 2012, 5 pages.
PCT International Preliminary Report on Patentability for PCT International Application No. PCT/GB2010/051529, mail date Apr. 5, 2012, 7 pages.
PCT International Preliminary Report on Patentability for PCT International Application No. PCT/GB2011/050368, mail date Sep. 13, 2012, 7 pages.
PCT International Search Report and Written Opinion of International Searching Authority for PCT International Application No. PCT/GB2011/050368, mail date Jun. 21, 2011, 11 pages.
PCT International Search Report and Written Opinion of International Searching Authority for PCT International Application No. PCT/GB2010/001232, mail date Oct. 6, 2010, 9 pages.
PCT International Preliminary Report on Patentability for PCT International Application No. PCT/GB2010/001232, mail date Jan. 4, 2012, 6 pages.
PCT International Search Report and Written Opinion of International Searching Authority for PCT International Application No. PCT/GB2010/051529, mail date Jan. 4, 2011, 11 pages.
PCT International Search Report for PCT International Application No. PCT/GB2013/051961; mailing date Dec. 11, 2013, (5 pgs.).

* cited by examiner

PROSTHETICS AND ORTHOTICS

CROSS REFERENCE TO RELATED APPLICATIONS

This is the national phase under 35 U.S.C. §371 of International Application No. PCT/GB2013/051961 filed on Jul. 23, 2013, which claims priority to and benefit of European Application No. 1213030.8 filed on Jul. 23, 2012, the entire disclosures of each of which are incorporated by reference herein.

The present invention relates to a prosthesis or an orthosis, particularly, but not exclusively, a hand prosthesis.

Prosthetic hands with powered digits are known. For example, WO 2007/063266 and WO 1995/24875 disclose a prosthesis with a mechanically operated digit member that is moved by an electric motor.

The present inventor has appreciated the shortcomings with known prostheses having motor driven digit members, such as those described in WO 2007/063266 and WO 1995/24875.

According to the present invention there is provided a prosthesis or an orthosis comprising:
 a moveable component having a motor operable to drive a worm gear; and
 a worm gear wheel fixedly mounted on a support member of the prosthesis or orthosis,
 wherein the moveable component extends generally tangentially with respect to the worm gear wheel and is mounted for rotation about the worm gear wheel, the worm gear being in engagement with the worm gear wheel such that, when the motor is operated in use of the prosthesis or orthosis, the moveable component rotates about the worm gear wheel,
 wherein one of the moveable component and the worm gear wheel or the support member includes at least one electrical contact member and the other of the moveable component and the worm gear wheel or the support member includes at least one electrical contact surface, the at least one electrical contact member and the at least one electrical contact surface being arranged to slidably contact one another as the moveable component rotates about the worm gear wheel.

In this arrangement the at least one electrical contact member slides along the at least one electrical contact surface maintaining a sliding electrical contact between the at least one electrical contact member and the at least one electrical contact surface as the moveable component rotates about the worm gear wheel.

The moveable component may be a digit of a hand prosthesis. The moveable component may be a digit member of a hand prosthesis. The component may be a finger member or a thumb member of a hand prosthesis.

The moveable component may comprise first and second digit members. The first and second digit members may be pivotably connected to one another. The first digit member may be coupled at its distal end to the second digit member to form a proximal joint for allowing movement of the second digit member in relation to the first digit member. The first digit member may be coupled to the second digit member with a coupling mechanism.

The moveable component may comprise a third digit member. The third digit member may be pivotably connected to the second digit member. The second digit member may be coupled at its distal end to the third digit member to form a distal joint for allowing movement of the third digit member in relation to the second digit member. The second digit member may be coupled to the third digit member with a coupling mechanism.

The moveable component may further comprise a housing. The motor may be positioned at least partially within the housing. The motor may be positioned at least partially within the moveable component.

The coupling mechanism between the first digit member and the second digit member may be located within the housing. The coupling mechanism between the second digit member and the third digit member may be located within the housing.

The housing may provide one or more channels for electrical wiring, or tracks, between the motor and the at least one electrical contact member or the at least one electrical contact surface.

The motor may include a drive shaft. The worm gear may be located on the drive shaft, such that operation of the drive shaft by the motor causes rotation of the worm gear. The worm gear may be arranged such that it rotates with the drive shaft of the motor but is at least partially axially moveable along the longitudinal axis of the drive shaft. The above arrangement allows some axial "play" between the worm gear and the worm gear wheel. Such play may be required to prevent excess loads being placed on the motor and thus preventing motor failure. A bearing may be located at the distal end of the motor drive shaft, such that the worm gear is located between the bearing and the motor. The bearing may have an inner race which is mounted to the motor drive shaft and an outer race which is mounted to the housing.

The motor may be an electric motor. The motor may be a direct current motor. The motor may be an AC motor, a brushed or brushless motor, a servo motor, a stepper motor, a linear motor or a worm gear motor.

The worm gear may be positioned at least partially within the moveable component. The worm gear may be positioned at least partially within the digit. The worm gear may be positioned at least partially within the first digit member. In this arrangement the rotational axis of the worm gear is substantially parallel to the rotational axis of the motor drive shaft. In this arrangement the rotational axis of the worm gear is also substantially coincident to the rotational axis of the motor drive shaft.

The worm gear may be positioned completely within the moveable component. The worm gear may be positioned completely within the digit. The worm gear may be positioned completely within the first digit member.

The worm gear may be positioned outside of the moveable component. The worm gear may be positioned outside of the digit. The worm gear may be positioned outside of the first digit member. The worm gear may be positioned outside of the housing of the moveable component.

The rotational axis of the worm gear may be inclined relative to the rotational axis of the motor drive shaft. The rotational axis of the worm gear may be substantially perpendicular to the rotational axis of the motor drive shaft. In this arrangement the moveable component may further comprise one or more transmission components to couple movement of the motor drive shaft to the worm gear. The one or more transmission components may include a bevelled gear arrangement. The bevelled gear arrangement may comprise a first bevel gear and a second bevel gear. The first and second bevel gears engage with each other, the first bevel gear being configured to move in response to movement of the motor drive shaft and the second bevel gear being coupled to the worm gear. The first and second bevel gears may be arranged such that they transmit rotation of the motor drive shaft and worm gear through approximately ninety degrees.

The moveable component may pivot about the worm gear wheel. The worm gear wheel may include an aperture for receiving a pivot shaft, or spindle. The moveable component may be mounted to the pivot shaft, or spindle. The housing of the moveable component may be mounted to the pivot shaft, or spindle.

The support member may be formed integrally with a main body of the prosthesis or orthosis. The support member may be formed separately from a main body of the prosthesis or orthosis and may be attachable thereto.

The support member may house one or more electrical connections for the operation of the motor. The support member may house one or more electrical power connections for the operation of the motor.

The at least one electrical contact member may be positioned on the moveable component and the at least one electrical contact surface may be positioned on the worm gear wheel or the support member. The at least one electrical contact member may be positioned on the first digit member of the moveable component and the at least one electrical contact surface may be positioned on the worm gear wheel or the support member.

The at least one electrical contact member may be positioned on the worm gear wheel or the support member and the at least one electrical contact surface may be positioned on the moveable component. The at least one electrical contact member may be positioned on the worm gear wheel or the support member and the at least one electrical contact surface may be positioned on the first digit member of the moveable component.

The at least one electrical contact member and the at least one electrical contact surface may be arranged such that, when the motor is operated in use of the prosthesis or orthosis, an electrical contact is maintained between the at least one electrical contact member and the at least one electrical contact surface as the moveable component rotates about the worm gear wheel. In this arrangement the at least one electrical contact member slides along the at least one electrical contact surface maintaining an electrical contact between the at least one electrical contact member and the at least one electrical contact surface as the moveable component rotates about the worm gear wheel.

The at least one electrical contact member may be biased towards the at least one electrical contact surface.

The at least one electrical contact member may comprise a pin member. The at least one electrical contact member may comprise a metal pin member. The pin member may be biased towards the at least one electrical contact surface. The pin member may be spring biased towards the at least one electrical contact surface. The pin member may comprise a substantially flat head portion which is arranged to contact the at least one electrical contact surface. The head portion may include a chamfered edge portion, or a curved edge portion. Alternatively, the pin member may comprise a dome-shaped head portion which is arranged to contact the at least one electrical contact surface. Alternatively, the at least one electrical contact member may comprise a brush or a sprung contact.

The at least one electrical contact member may be housed in a housing. The housing may be positioned in the moveable component, the worm gear wheel or the support member. The housing may include one or more biasing devices for biasing the at least one electrical contact member towards the at least one electrical contact surface.

The at least one electrical contact surface may be an elongate track. The at least one electrical contact surface may be an elongate metal track. The at least one electrical contact surface may be in the shape of an arc. The at least one electrical contact surface may be arc-shaped. The shape and length of the at least one electrical contact surface is arranged to follow the path of the moveable component as it rotates about the worm gear wheel. The shape and length of the at least one electrical contact surface is arranged to follow the path of the at least one electrical contact member as it rotates about the worm gear wheel.

At least a part of the at least one electrical contact surface may be etched onto the moveable component, the worm gear wheel or the support member.

At least a part of the at least one electrical contact surface may be provided on a support member. The support member may be a sheet. At least a part of the at least one electrical contact surface may be provided on a flexible sheet. The flexible sheet may be positioned on the moveable component, the worm gear wheel or the support member. The flexible sheet may be fixedly attached to the moveable component, the worm gear wheel or the support member. The flexible sheet may be fixedly attached to the moveable component, the worm gear wheel or the support member with one or more adhesives.

The at least one electrical contact surface may include one or more electrical connections for operation of the motor. The at least one electrical contact surface may include one or more electrical power connections for operation of the motor. The one or more electrical connections of the at least one electrical contact surface may be arranged to connect with the one or more electrical connections of the support member.

The at least one electrical contact surface may provide electrical power to the motor via the at least one electrical contact member. The at least one electrical contact surface may be connected to an electrical power source. The at least one electrical contact surface may be connected to an electrical power source via one or more electrical wires, or tracks. The electrical power source may include one or more batteries. The at least one electrical contact member may be electrically connected to the motor. The at least one electrical contact member may be electrically connected to the motor via one or more electrical wires, or tracks.

The at least one electrical contact surface may provide AC or DC electrical power to the motor via the at least one electrical contact member.

The prosthesis or orthosis may include two electrical contact members and two electrical contact surfaces. The prosthesis or orthosis may include a third electrical contact member and a third electrical contact surface. The two electrical contact surfaces may provide AC or DC electrical power to the motor via the two electrical contact members. In this arrangement a first electrical contact member is arranged to be in sliding contact with a first electrical contact surface and a second electrical contact member is arranged to be in sliding contact with a second electrical contact surface. In this arrangement the first and second electrical contact surfaces may be arranged to alternate between a positive and negative potential voltage difference. Alternatively, one of the first or second electrical contact surfaces may be arranged to be held at a zero potential voltage difference, i.e. electrically grounded. In this arrangement the first and second electrical contact members supply AC or DC electrical power to the motor. The third electrical contact surface may be held at zero potential difference, i.e. electrically grounded. The third electrical contact member may be arranged to be in sliding contact with the third electrical contact surface. The first and second electrical contact members may be electrically connected to the input terminals of the motor by electrical wires, etched tracks, or the like. The third electrical contact member may be electrically connected to the input terminals of the motor by electrical wires, etched tracks, or the like.

The first and second electrical contact members may be housed in a housing. The first electrical contact member may be housed in a first housing and the second electrical contact member may be housed in a second housing. The third electrical contact member may be housed in the first or second housing. The first and second housings may be positioned in one of the moveable component and the worm gear wheel or the support member. The first and second electrical contact surfaces may be provided in the other of the moveable component and the worm gear wheel or the support member.

The first and second electrical contact surfaces may be located on the worm gear wheel. The third electrical contact surface may be located on the worm gear wheel.

The first and second electrical contact surfaces may be located on the same side of the worm gear wheel and the first and second electrical contact members may be located on the same side of the moveable component. The first and second electrical contact surfaces may be located on opposite sides of the worm gear wheel and the first and second electrical contact members may be located on opposing sides of the moveable component. The third electrical contact surface may be located on either side of the worm gear wheel. In this arrangement the worm gear wheel is sandwiched between the first, second and third electrical contact members. In this arrangement AC or DC electrical power is supplied from a battery or power source to the motor via electrical connections in the support member, electrical connections on the electrical contact surfaces and the electrical contact members.

The prosthesis or orthosis may further comprise a position sensing device for sensing the position of the moveable component relative to the worm gear wheel or the support member.

The position sensing device may be operable to produce an output signal indicative of the position of the moveable component relative to the worm gear wheel or the support member. The output signal may be an encoded signal.

The position sensing device may include an encoder, the encoder being operable to produce an output signal indicative of the position of the moveable component relative to the worm gear wheel or the support member.

The position sensing device may include at least one electrical contact member and at last one electrical contact surface. The least one electrical contact member may be positioned on one of the moveable component and the worm gear wheel or the support member and the at least one electrical contact surface may be positioned on the other of the moveable component and the worm gear wheel or the support member. The at least one electrical contact member and the at least one electrical contact surface being arranged such that a sliding contact is maintained between the at least one electrical contact member and the at least one electrical contact surface as the moveable component rotates about the worm gear wheel. That is, the at least one electrical contact member and the at least one electrical contact surface being arranged to slidably contact one another as the moveable component rotates about the worm gear wheel.

The position sensing device may include two electrical contact members and two electrical contact surfaces.

The at least one electrical contact member of the position sensing device may be positioned on the moveable component and the at least one electrical contact surface of the position sensing device may be positioned on the worm gear wheel or the support member. The at least one electrical contact member of the position sensing device may be positioned on the first digit member of the moveable component and the at least one electrical contact surface of the position sensing device may be positioned on the worm gear wheel or the support member.

The at least one electrical contact member of the position sensing device may be positioned on the worm gear wheel or the support member and the at least one electrical contact surface of the position sensing device may be positioned on the moveable component. The at least one electrical contact member of the position sensing device may be positioned on the worm gear wheel or the support member and the at least one electrical contact surface of the position sensing device may be positioned on the first digit member of the moveable component.

The at least one electrical contact member of the position sensing device and the at least one electrical contact surface of the position sensing device may be arranged such that, when the motor is operated in use of the prosthesis or orthosis, an electrical contact is maintained between the at least one electrical contact member of the position sensing device and the at least one electrical contact surface of the position sensing device as the moveable component rotates about the worm gear wheel. In this arrangement the at least one electrical contact member of the position sensing device slides along the at least one electrical contact surface of the position sensing device maintaining an electrical contact between the at least one electrical contact member of the position sensing device and the at least one electrical contact surface of the position sensing device as the moveable component rotates about the worm gear wheel.

The at least one electrical contact member of the position sensing device may be biased towards the at least one electrical contact surface of the position sensing device.

The at least one electrical contact member of the position sensing device may comprise a pin member. The at least one electrical contact member of the position sensing device may comprise a metal pin member. The pin member may be biased towards the at least one electrical contact surface of the position sensing device. The pin member may be spring biased towards the at least one electrical contact surface of the position sensing device. The pin member may comprise a substantially flat head portion which is arranged to contact the at least one electrical contact surface of the position sensing device. The head portion may include a chamfered edge portion, or a curved edge portion. Alternatively, the pin member may comprise a dome-shaped head portion which is arranged to contact the at least one electrical contact surface of the position sensing device. Alternatively, the at least one electrical contact member may comprise a brush or a sprung contact.

The at least one electrical contact member of the position sensing device may be housed in a housing. The housing may be positioned in the moveable component, the worm gear wheel or the support member. The housing may include one or more biasing devices for biasing the at least one electrical contact member of the position sensing device towards the at least one electrical contact surface of the position sensing device.

The at least one electrical contact surface of the position sensing device may be an elongate track. The at least one electrical contact surface of the position sensing device may be an elongate metal track. The at least one electrical contact surface of the position sensing device may be in the shape of an arc. The at least one electrical contact surface of the position sensing device may be arc-shaped. The shape and length of the at least one electrical contact surface of the position sensing device is arranged to follow the path of the moveable component as it rotates about the worm gear wheel. The shape and length of the at least one electrical contact surface of the position sensing device is arranged to follow the path of the at least one electrical contact member of the position sensing device as it rotates about the worm gear wheel.

The at least one electrical contact surface of the position sensing device may be at least partially etched onto the moveable component, the worm gear wheel or the support member.

At least a part of the at least one electrical contact surface of the position sensing device may be provided on a support member. The support member may be a sheet. At least a part of the at least one electrical contact surface of the position sensing device may be provided on a flexible sheet. The flexible sheet may be positioned on the moveable component, the worm gear wheel or the support member. The flexible sheet may be fixedly attached to the moveable component, the worm gear wheel or the support member. The flexible sheet may be fixedly attached to the moveable component, the worm gear wheel or the support member with one or more adhesives.

The at least one electrical contact surface of the position sensing device may include one or more electrical connections for operation of the position sensing device. The at least one electrical contact surface of the position sensing device may include one or more electrical power connections for operation of the position sensing device. The one or more electrical connections of the at least one electrical contact surface of the position sensing device may be arranged to connect with the one or more electrical connections of the support member.

The at least one electrical contact surface of the position sensing device may comprise a first contact surface and a second contact surface. The first contact surface may be an elongate track. The second contact surface may be an elongate track. The first and second elongate tracks may be in the shape of an arc. The first and second elongate tracks may be arc-shaped. The shape and length of the first and second elongate tracks are generally arranged to follow the path of the moveable component as it rotates about the worm gear wheel. The shape and length of the first and second elongate tracks are generally arranged to follow the path of the at least one electrical contact member of the position sensing device as it rotates about the worm gear wheel.

The first contact surface and a second contact surface of the position sensing device may be electrically isolated from one another. The first and second elongate tracks of the position sensing device may be electrically isolated from one another.

The first contact surface and the second contact surface of the position sensing device may be arranged such that the at least one electrical contact member of the position sensing device alternately electrically connects and electrically disconnects the first contact surface and the second contact surface as the at least one electrical contact member rotates about the worm gear wheel. The first and second elongate tracks of the position sensing device may be arranged such that the at least one electrical contact member of the position sensing device alternately electrically connects and electrically disconnects the first contact surface and the second contact surface as the at least one electrical contact member rotates about the worm gear wheel.

The at least one electrical contact member of the position sensing device may be arranged to always be in electrical contact with at least one of the first contact surface and the second contact surface of the position sensing device. However, it should be appreciated that the at least one electrical contact member of the position sensing device may not necessarily always be in electrical contact with at least one of the first contact surface and the second contact surface of the position sensing device. For example, the at least one electrical contact member of the position sensing device may not necessarily have to be in electrical contact with the first contact surface and the second contact surface of the position sensing device as the moveable component rotates about the worm gear wheel. It is possible that the at least one electrical contact member may be in physical contact with the worm gear wheel and not necessarily make an electrical contact with first contact surface and the second contact surface of the position sensing device.

The first and second elongate tracks of the position sensing device may at least partially overlap in the direction of the path of the at least one electrical contact member as it rotates about the worm gear wheel. The partially overlapping areas of the first and second elongate tracks may include an area of equal spacing between the first and second tracks. The partially overlapping areas of the first and second elongate tracks may include an area where the spacing between the first and second tracks reduces gradually. The partially overlapping areas of the first and second elongate tracks may include an area where the spacing between the first and second tracks increases gradually.

The at least one electrical contact surface of the position sensing device may be connected to an electrical power source. The at least one electrical contact surface of the position sensing device may be connected to an electrical power source via one or more electrical wires, or tracks. The electrical power source may include one or more batteries.

The first and second elongate tracks of the position sensing device may be connected to an electrical power source. The electrical power source may be an AC or DC electrical power source. The first and second elongate tracks of the position sensing device may be arranged to alternate between a positive and negative potential voltage difference. Alternatively, one of the first or second elongate tracks may be arranged to be held at a zero potential voltage difference, i.e. electrically grounded. In this arrangement the at least one electrical contact member completes the electric circuit between the first and second elongate tracks when it contacts both the first and second elongate track as it rotates about the worm gear wheel. The circuit is broken when the at least one electrical contact member does not contact both the first and second elongate track. In this arrangement the position sensing device outputs an encoded signal in the form of a series of spaced apart voltage pulses. The output signal is indicative of the position of the moveable component relative to the worm gear wheel.

The at least one electrical contact member of the position sensing device may be housed in a housing. The housing may be positioned in one of the moveable component and the worm gear wheel or the support member. The first and second elongate tracks of the position sensing device may be provided in the other of the moveable component and the worm gear wheel or the support member.

The first and second elongate tracks of the position sensing device may be located on the worm gear wheel.

The first and second elongate tracks of the position sensing device may be located on the same side of the worm gear wheel.

The position sensing device may further comprise an indicator device which may be arranged to output a signal to the user of the prosthesis or orthosis if the position of the moveable component relative to the worm gear wheel or the support member moves to an undesired position.

The indicator device may output the signal to the user when the at least one electrical contact member of the position sensing device enters the area where the spacing between the first and second tracks reduces gradually or increases gradually, or where the spacing between the first and second tracks is less than or greater than a main operational area.

The support member may house one or more electrical connections for the operation of the position sensing device.

The position sensing device may include at least one optical reading member and at last one optically readable surface. The least one optical reading member may be positioned on one of the moveable component and the worm gear wheel or the support member and the at least one optically readable surface may be positioned on the other of the moveable component and the worm gear wheel or the support member. The at least one optical reading member and the at least one optically readable surface being arranged such that the at least one optical reading member is capable of optically reading the surface of the at least one optically readable surface as the moveable component rotates about the worm gear wheel.

The at least one optical reading member of the position sensing device may be positioned on the moveable component and the at least one optically readable surface of the position sensing device may be positioned on the worm gear wheel or the support member. The at least one optical reading member of the position sensing device may be positioned on the first digit member of the moveable component and the at least one optically readable surface of the position sensing device may be positioned on the worm gear wheel or the support member.

The at least one optical reading member of the position sensing device may be positioned on the worm gear wheel or the support member and the at least one optically readable surface of the position sensing device may be positioned on the moveable component. The at least one optical reading member of the position sensing device may be positioned on the worm gear wheel or the support member and the at least one optically readable surface of the position sensing device may be positioned on the first digit member of the moveable component.

The at least one optical reading member of the position sensing device and the at least one optically readable surface of the position sensing device may be arranged such that, when the motor is operated in use of the prosthesis or orthosis, the at least one optical reading member is capable of optically reading the surface of the at least one optically readable surface as the moveable component rotates about the worm gear wheel. In this arrangement the at least one optical reading member of the position sensing passes over the at least one optically readable surface of the position sensing device as the moveable component rotates about the worm gear wheel.

The at least one optical reading member of the position sensing device may be housed in a housing. The housing may be positioned in the moveable component, the worm gear wheel or the support member.

The at least one optically readable surface of the position sensing device may be an elongate track. The at least one optically readable surface of the position sensing device may be in the shape of an arc. The at least one optically readable surface of the position sensing device may be arc-shaped. The shape and length of the at least one optically readable surface of the position sensing device is arranged to follow the path of the moveable component as it rotates about the worm gear wheel. The shape and length of the at least one optically readable surface of the position sensing device is arranged to follow the path of the at least one optical reading member of the position sensing device as it rotates about the worm gear wheel.

At least a part of the at least one optically readable surface of the position sensing device may be provided on a flexible sheet. The flexible sheet may be positioned on the moveable component, the worm gear wheel or the support member. The flexible sheet may be fixedly attached to the moveable component, the worm gear wheel or the support member. The flexible sheet may be fixedly attached to the moveable component, the worm gear wheel or the support member with one or more adhesives.

The at least one optically readable surface of the position sensing device may include one or more electrical connections for operation of the position sensing device. The at least one optically readable surface of the position sensing device may include one or more electrical power connections for operation of the position sensing device. The one or more electrical connections of the at least one optically readable surface of the position sensing device may be arranged to connect with the one or more electrical connections of the support member.

The at least one optically readable surface of the position sensing device may comprise one or more optically readable patterns.

The at least one optically readable surface of the position sensing device may be arranged such that an alternate light/dark signal is read by the at least one optical reading member as the at least one optical reading member rotates about the worm gear wheel.

The at least one optical reading member may include a photocell. The at least one optically readable surface and the at least one optical reading member may include a photoemitter-detector pair.

The at least one optically readable surface may include a main operational area where the optically readable pattern does not change and a smaller operational area where the optically readable pattern is different to that of the main operational area.

The position sensing device outputs an encoded signal in the form of a series of spaced apart pulses. The output signal is indicative of the position of the moveable component relative to the worm gear wheel.

The position sensing device may further comprise an indicator device which may be arranged to output a signal to the user of the prosthesis or orthosis if the position of the moveable component relative to the worm gear wheel or the support member moves to an undesired position.

The indicator device may output the signal to the user when the at least one optical reading member of the position sensing device enters the smaller operational area where the optical pattern of the optically readable surface differs from the main operational area.

The position sensing device may include at least one magnetic reading member and at last one magnetically readable surface. The least one magnetic reading member may be positioned on one of the moveable component and the worm gear wheel or the support member and the at least one magnetically readable surface may be positioned on the other of the moveable component and the worm gear wheel or the support member. The at least one magnetic reading member and the at least one magnetically readable surface being arranged such that the at least one magnetic reading member is capable of magnetically reading the surface of the at least one magnetically readable surface as the moveable component rotates about the worm gear wheel.

The at least one magnetic reading member of the position sensing device may be positioned on the moveable component and the at least one magnetically readable surface of the position sensing device may be positioned on the worm gear wheel or the support member. The at least one magnetic reading member of the position sensing device may be positioned on the first digit member of the moveable component and the at least one magnetically readable surface of the position sensing device may be positioned on the worm gear wheel or the support member.

The at least one magnetic reading member of the position sensing device may be positioned on the worm gear wheel or the support member and the at least one magnetically readable surface of the position sensing device may be positioned on the moveable component. The at least one magnetic reading member of the position sensing device may be positioned on the worm gear wheel or the support member and the at least one magnetically readable surface of the position sensing device may be positioned on the first digit member of the moveable component.

The at least one magnetic reading member of the position sensing device and the at least one magnetically readable surface of the position sensing device may be arranged such that, when the motor is operated in use of the prosthesis or orthosis, the at least one magnetic reading member is capable of magnetically reading the surface of the at least one magnetically readable surface as the moveable component rotates about the worm gear wheel. In this arrangement the at least one magnetic reading member of the position sensing passes over the at least one magnetically readable surface of the position sensing device as the moveable component rotates about the worm gear wheel.

The at least one magnetic reading member of the position sensing device may be housed in a housing. The housing may be positioned in the moveable component, the worm gear wheel or the support member.

The at least one magnetically readable surface of the position sensing device may be an elongate track. The at least one magnetically readable surface of the position sensing device may be in the shape of an arc. The at least one magnetically readable surface of the position sensing device may be arc-shaped. The shape and length of the at least one magnetically readable surface of the position sensing device is arranged to follow the path of the moveable component as it rotates about the worm gear wheel. The shape and length of the at least one magnetically readable surface of the position sensing device is arranged to follow the path of the at least one magnetic reading member of the position sensing device as it rotates about the worm gear wheel.

At least a part of the at least one magnetically readable surface of the position sensing device may be provided on a flexible sheet. The flexible sheet may be positioned on the moveable component, the worm gear wheel or the support member. The flexible sheet may be fixedly attached to the moveable component, the worm gear wheel or the support member. The flexible sheet may be fixedly attached to the moveable component, the worm gear wheel or the support member with one or more adhesives.

The at least one magnetically readable surface of the position sensing device may include one or more electrical connections for operation of the position sensing device. The at least one magnetically readable surface of the position sensing device may include one or more electrical power connections for operation of the position sensing device. The one or more electrical connections of the at least one magnetically readable surface of the position sensing device may be arranged to connect with the one or more electrical connections of the support member.

The at least one magnetically readable surface of the position sensing device may comprise one or more magnetically readable patterns.

The at least one magnetically readable surface of the position sensing device may be arranged such that an alternating magnetic field is read by the at least one magnetic reading member as the at least one magnetic reading member rotates about the worm gear wheel. The at least one magnetically readable surface of the position sensing device may be arranged such that changes in a magnetic field is read by the at least one magnetic reading member as the at least one magnetic reading member rotates about the worm gear wheel.

The at least one magnetic reading member may include a permanent magnet. The at least one magnetically readable surface and the at least one magnetic reading member may include a ferrous metal and a magnetic pick-up that contains a permanent magnet.

The at least one magnetically readable surface may include a main operational area where the magnetically readable surface does not change and a smaller operational area where the magnetically readable surface is different to that of the main operational area.

The position sensing device outputs an encoded signal in the form of a series of spaced apart pulses. The output signal is indicative of the position of the moveable component relative to the worm gear wheel.

The position sensing device may further comprise an indicator device which may be arranged to output a signal to the user of the prosthesis or orthosis if the position of the moveable component relative to the worm gear wheel or the support member moves to an undesired position.

The indicator device may output the signal to the user when the at least one magnetic reading member of the position sensing device enters the smaller operational area where the magnetic pattern of the magnetically readable surface differs from the main operational area.

The prosthesis or orthosis may further comprise an electronic device. The electronic device may be configured to control the operation of the motor. The electronic device may be configured to decode the output signal from the position sensing device to determine the position of the moveable component with respect to the worm gear wheel or the support member.

The motor may be operable via one or more switches. The switches may be actuated by residual movement of the wearer of the prosthesis or orthosis, wrist and/or shoulder movement of the wearer of the prosthesis or orthosis, or the like. Alternatively, or additionally, the motor may be operable via signals derived from the activity of, or from, electromyographic (EMG) activity of residual muscle actions of the wearer of the prosthesis or orthosis, pressure sensitive resistors on the wearer of the prosthesis or orthosis, signals derived from one or more neural implants in the wearer of the prosthesis or orthosis, EMG activity from reinnervated muscles, muscles of the feet and/or chest, or the like.

The prosthesis or orthosis may comprise a plurality of moveable components and worm gear wheels. Each moveable component having a motor operable to drive a worm gear and each worm gear wheel fixedly mounted on a support member. The moveable components each extending generally tangentially with respect to their respective worm gear wheel and each being mounted for rotation about their respective worm gear wheel, each worm gear being in engagement with the respective worm gear wheel such that, when the motor is operated in use, the moveable component rotates about the worm gear wheel, wherein for each moveable component and worm gear wheel pair one of the moveable component and the worm gear wheel or the support member includes at least one electrical contact member and the other of the moveable component and the worm gear wheel or the support member includes at least one electrical contact surface, the at least one electrical contact member and the at least one electrical contact surface being arranged to slidably contact one another as the moveable component rotates about the worm gear wheel.

An embodiment of the present invention will now be described, by way of example only, with reference to the accompanying drawings, in which.

Figure 1:
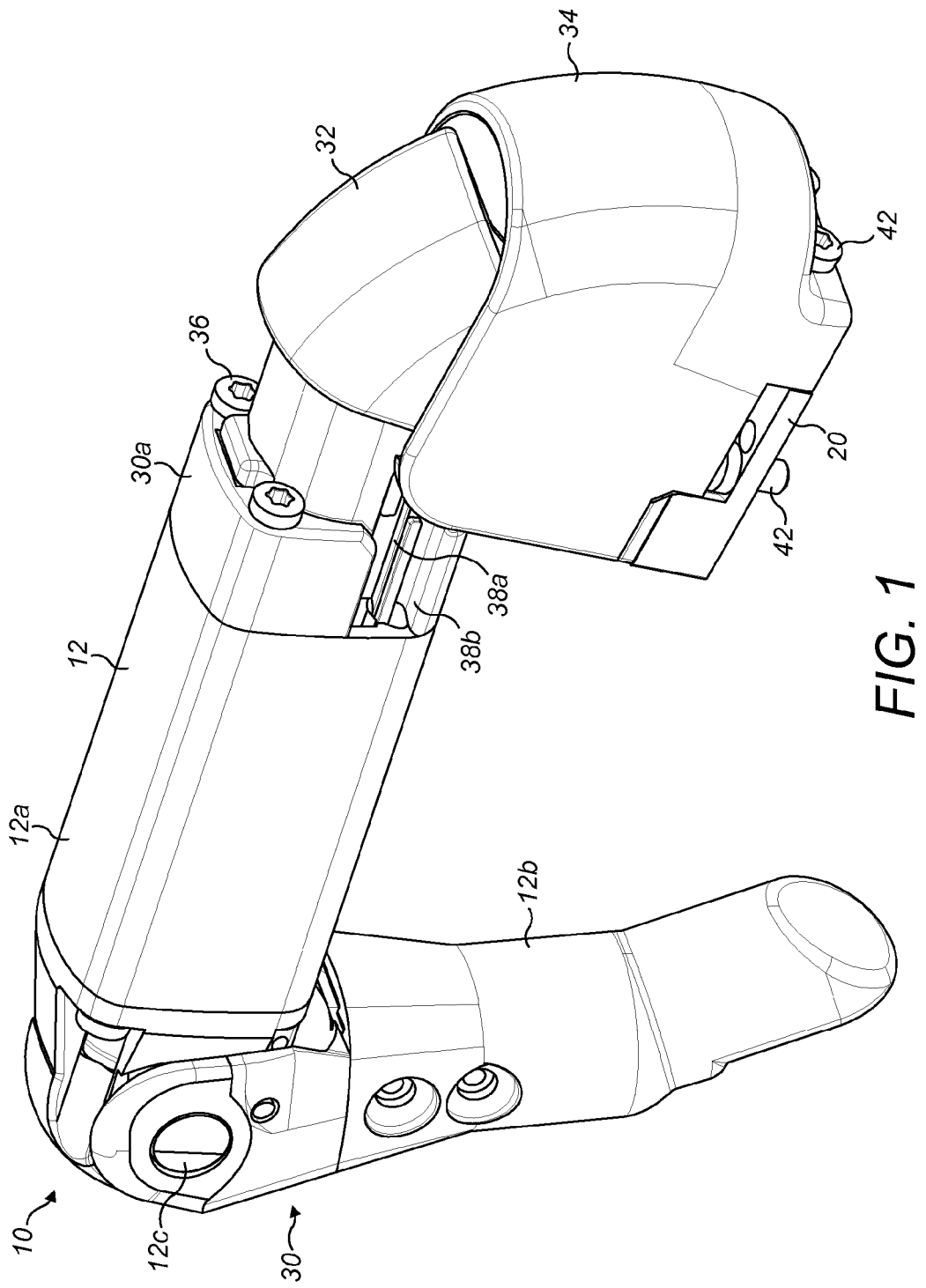
FIG. 1 is a perspective view of a hand prosthesis according to the present invention.
Figure 2:
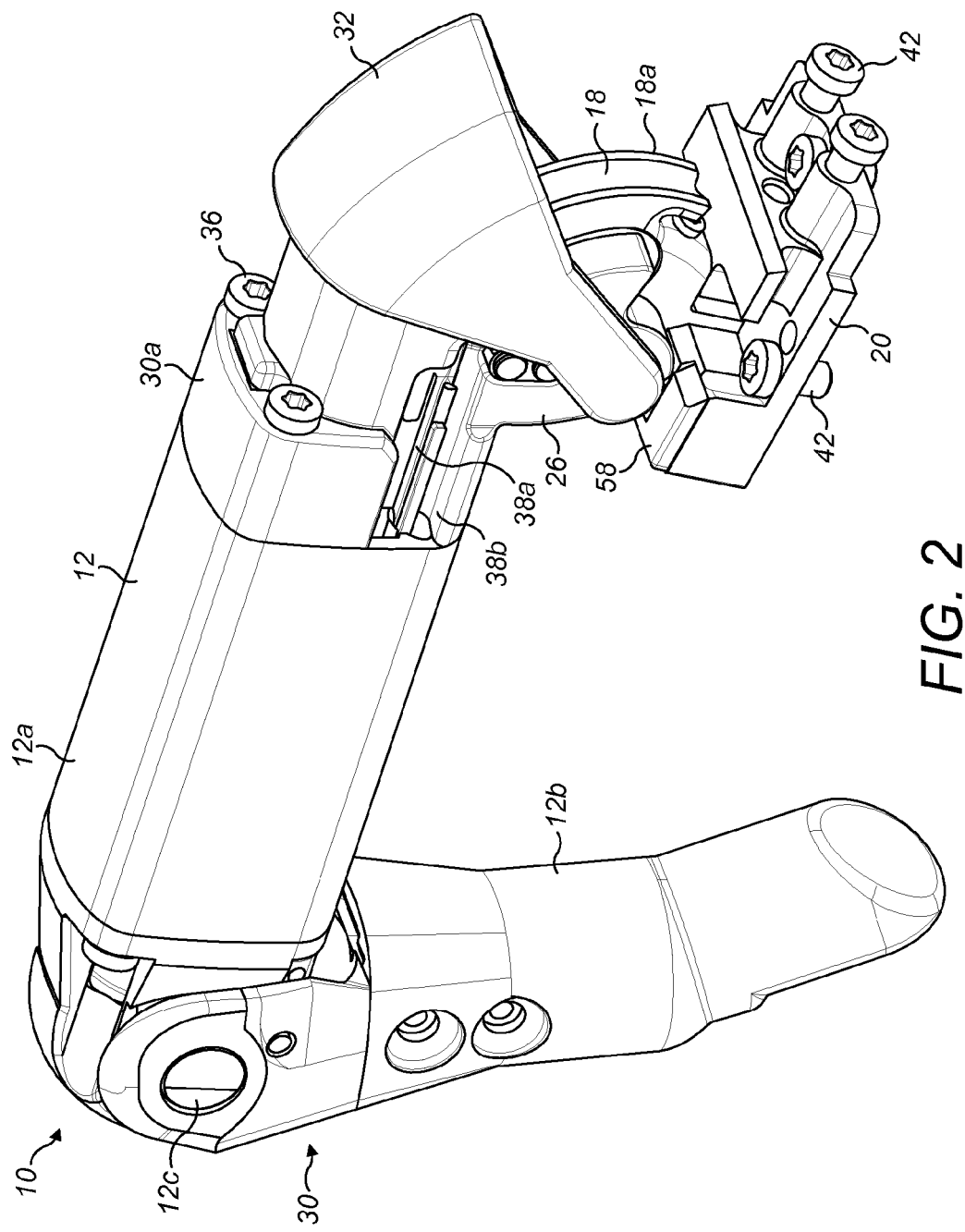
FIG. 2 is a perspective view of the hand prosthesis of FIG. 1 with a part of a cover member removed.

FIGS. 1 to 5 illustrate a hand prosthesis 10. The hand prosthesis 10 comprises a moveable component 12. The moveable component 12 has a motor 14. The motor 14 is operable to drive a worm gear 16. The hand prosthesis 10 also comprises a worm gear wheel 18. The worm gear wheel 18 is fixedly mounted on a support member 20.

Figure 3:
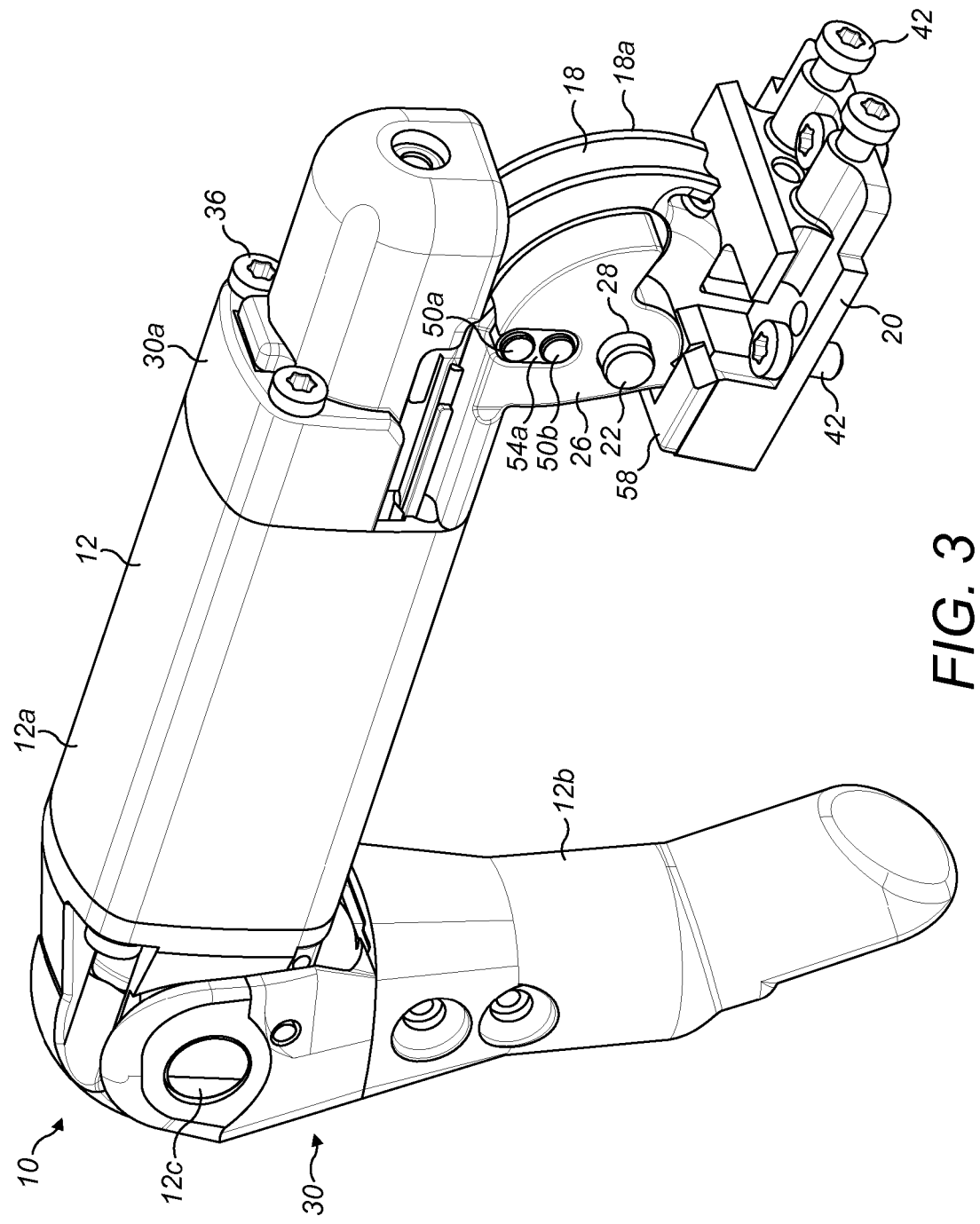
FIG. 3 is a perspective view of the hand prosthesis of FIG. 2 with a further part of a cover member removed.

The moveable component 12 extends generally tangentially with respect to the worm gear wheel 18 and is mounted for rotation about the worm gear wheel 18. As best illustrated in FIG. 3, the moveable component 12 is connected with the worm gear wheel 18 via a pivot member 22. The pivot member 22 is a cylindrical rod which passes through a circular aperture 24 in the worm gear wheel 18. The moveable component has a pair of lugs 26 which have circular apertures 28 which receive the pivot member 22 therein.

The worm gear 16 is in engagement with the worm gear wheel 18 such that, when the motor 14 is operated in use of the hand prosthesis 10, the moveable component 12 rotates about the worm gear wheel 18.

The moveable component 12 comprises a first digit member 12a and a second digit member 12b. The first and second digit members 12a and 12b are pivotably connected to one another. The first digit member 12a is coupled at its distal end to the second digit member 12b to form a proximal joint 12c for allowing movement of the second digit member 12b in relation to the first digit member 12a. The first digit member 12a is coupled to the second digit member 12b with a coupling mechanism (not illustrated). The coupling mechanism is arranged such that, when the moveable component 12 rotates about the worm gear wheel 18, the second digit member 12b pivots with respect to the first digit member 12a. The coupling mechanism includes one or more cables which are connected to the second digit member 12b and the worm gear wheel 18 or support member 20. In this arrangement, when the first digit member 12a pivots with respect to the worm gear wheel 18, the one or more cables of the coupling mechanism either pull the second digit member 12b towards the worm gear wheel 18, i.e. a movement which mimics the closing of a finger of a human hand, or moves the second digit 12b away from the worm gear wheel 18, i.e. a movement which mimics the extension of a finger of a human hand. (Note: the second digit member 12b is preferably spring biased towards an extended position relative to the first digit member 12a).

The moveable component 12 comprises a housing, generally illustrated by the reference number 30. The housing 30 comprises a number of components which form the outer shell of the moveable component 12. The hand prosthesis 10 also includes cover components 32 and 34. Cover components 32 and 34 are arranged to cover at least a portion of the worm gear wheel 18 and support member 20. The cover components 32 and 34 generally correspond to the knuckle portion (metacarpophalangeal joint) of a human hand.

As best illustrated in FIG. 3, the housing 30 includes a proximal housing 30a. The proximal housing 30a houses the worm gear 16 and part of the motor 14 therein. In this arrangement the worm gear 16 and motor 14 are considered as being positioned within the first digit member 12a. The proximal housing 30a is fixedly attached to the housing 30 via bolts 36. The proximal housing 30a is also arranged to at least partially receive the worm gear wheel 18 therein. The proximal housing 30a includes the pair of lugs 26. The worm gear wheel 18 is positioned between the lugs 26 and the apertures 24 and 28 are aligned such that the pivot member 22 can be fitted therethrough. The proximal housing 30a and the housing 30 include channels 38a for electrical wiring (not illustrated) between the motor 14 and the electrical contact member or the electrical contact surface (see below) and channels 38b for the cables (not illustrated) of the coupling mechanism, as described above.

Figure 4:
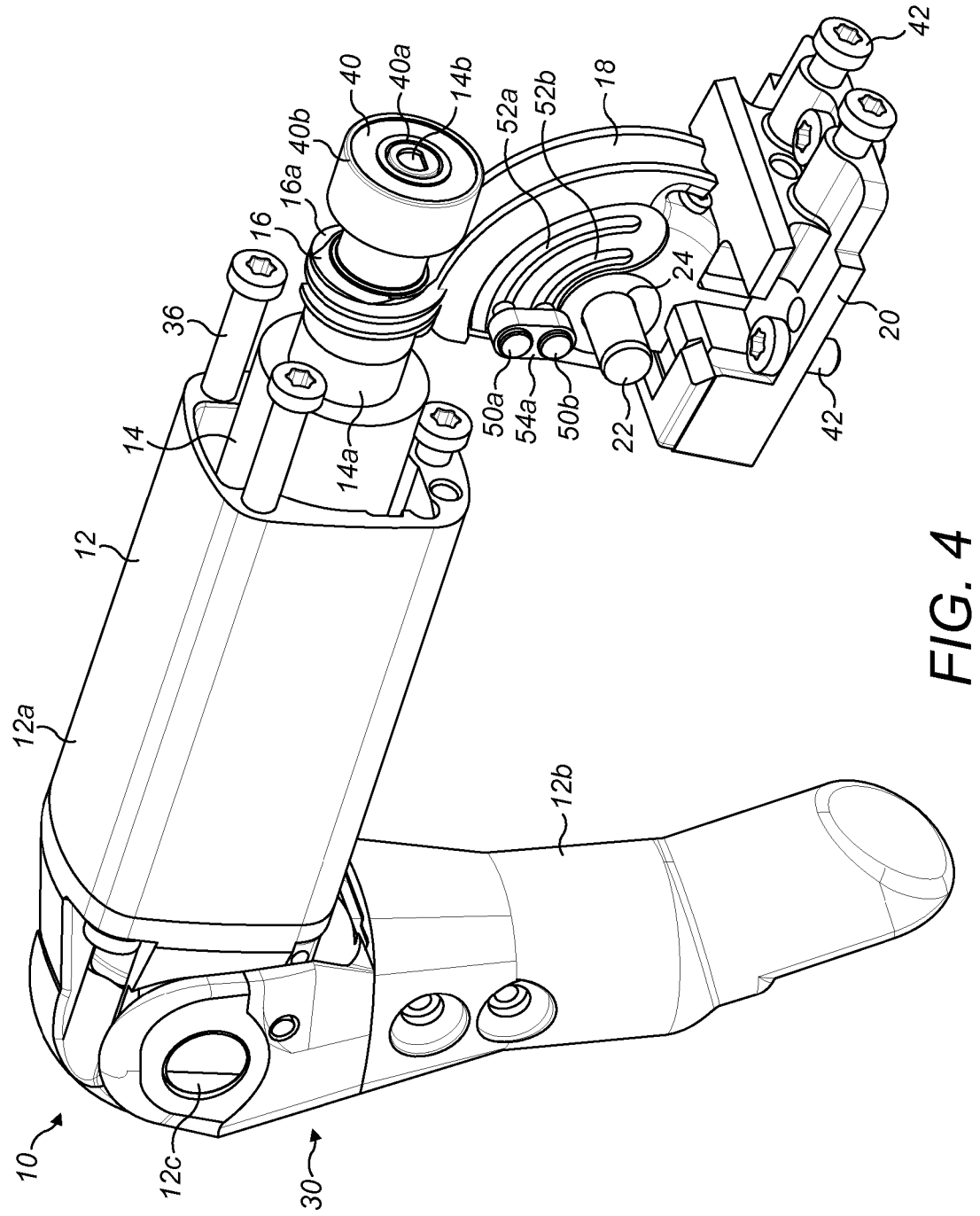
FIG. 4 is a perspective view of the hand prosthesis of FIG. 3 with a part of the digit housing removed.
Figure 5:
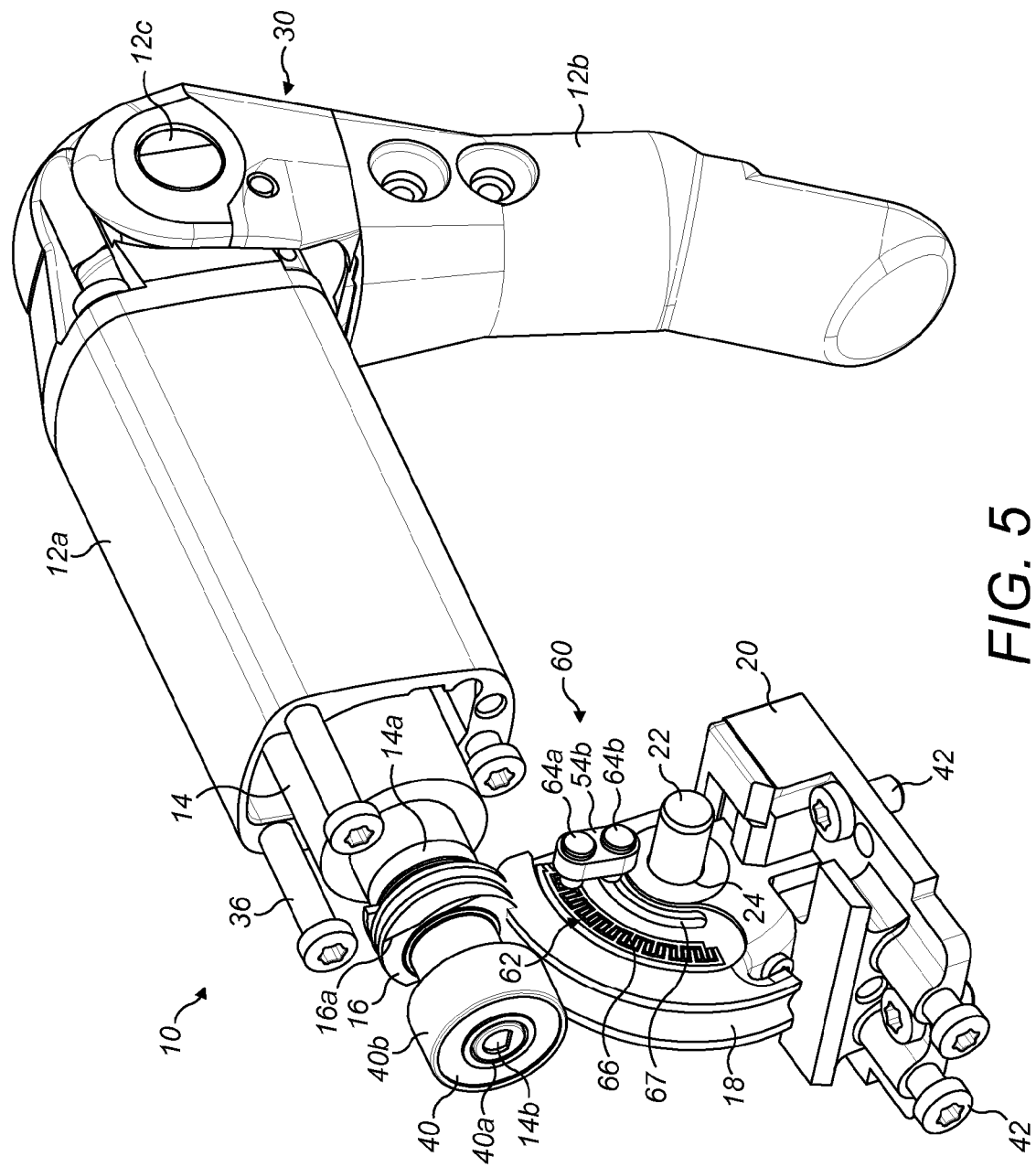
FIG. 5 is an opposite perspective view of the hand prosthesis of FIG. 4.
Figure 6:
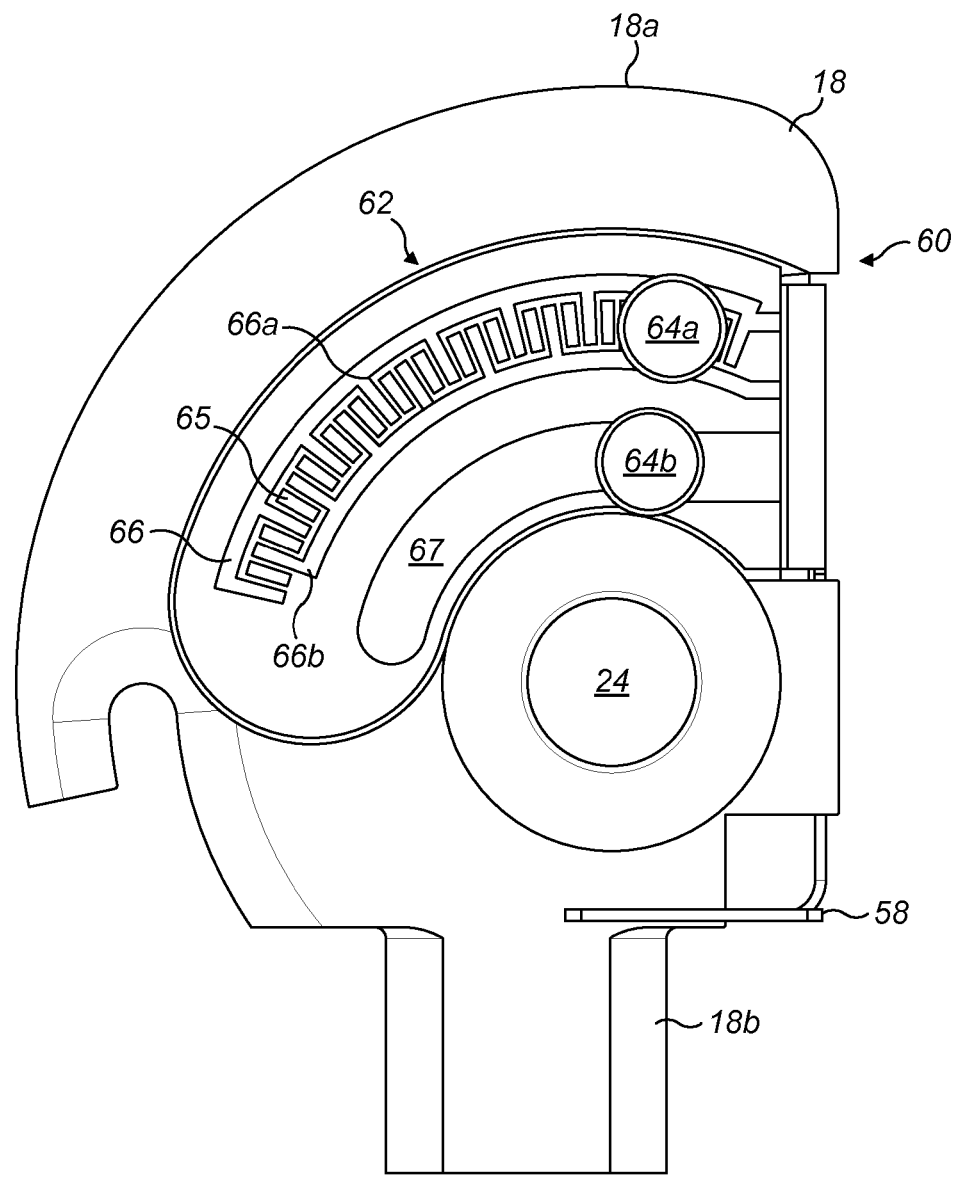
FIG. 6 is a side view of the worm gear wheel of the hand prosthesis of FIG. 1.

As best illustrated in FIGS. 4 and 5, the motor 14, which is an electric motor, is positioned within the housing 30. Although not illustrated, the coupling mechanism is also positioned within the housing 30.

With reference to FIGS. 4 and 5, the motor 14 includes a drive shaft housing 14a and motor drive shaft 14b. The worm gear 16 is located on the drive shaft 14b, such that operation of the drive shaft 14b by the motor 14 causes rotation of the worm gear 16. In this arrangement the rotational axis of the worm gear 16 is substantially parallel and coincident with the rotational axis of the drive shaft 14b of the motor 14. The worm gear 16 is arranged to engage with the worm gear wheel 18. The teeth 16a of the worm gear 16 are arranged to engage with the teeth 18a of the worm gear wheel 18. (Note: the specific teeth 18a of the worm gear wheel 18 have not been illustrated. However, it should be appreciated that the gear teeth are of the normal arrangement that engage and work with a worm gear.) A bearing 40 is positioned at the distal end of the drive shaft 14b. The bearing has an inner race 40a which is mounted to the drive shaft 14b and an outer race 40b which is mounted to an inner surface of the proximal housing 30a.

The worm gear 16 is arranged on the drive shaft 14b such that it is rotatable with the drive shaft 14b. The worm gear 16 is also arranged such that it is at least partially moveable along the drive shaft 14b (i.e. at least partially axially moveable along the drive shaft 14b of the motor 14). As illustrated in FIGS. 4 and 5, the drive shaft 14b has a D-shaped cross section portion which matches with a correspondingly shaped portion of the worm gear 16. This arrangement provides the axial "play" between the worm gear 16 and the drive shaft 14*b*.

The support member 20 is arranged such that it is attachable to a main body of a prosthesis (not illustrated). The support member 20 is attachable to the main body of the prosthesis via attachment bolts 42. As best illustrated in FIGS. 1 to 5, the support member 20 is used to house and provide support to the worm gear wheel 18. The support member 20 also houses a number of electrical power connections for the operation of the motor 14 and a position sensing device (see below).

The worm gear wheel 18 is a generally disc-shaped component with a roughly quarter-circular profile. The gear teeth 18*a* are located on the outer circumference of the worm gear wheel 18. As described above, a circular aperture 24 is provided towards the centre of the worm gear wheel 18. The circular aperture 24 receives the pivot member 22 therethrough. The worm gear wheel 18 also includes a mounting portion 18*b* located towards the bottom of the worm gear wheel 18. The mounting portion 18*b* is received by the support member 20. The mounting portion 18*b* includes a fastening attachment aperture 18*c* which is used to fasten the worm gear wheel 18 to the support member 20. The worm gear wheel 18 is fastened to the support member 20 via a bolt 48.

As illustrated in FIGS. 3 to 7, the moveable component 12 includes two electrical contact members 50*a* and 50*b* and the worm gear wheel 18 includes two electrical contact surfaces 52*a* and 52*b*. The electrical contact members 50*a*, 50*b* and the electrical contact surfaces 52*a*, 52*b* are used to supply electrical power to the motor 14. The electrical contact members 50*a*, 50*b* are connected to the terminal inputs of the motor via electrical wires (not illustrated). The electrical contact surfaces 52*a*, 52*b* are connected to an electrical power source (not illustrated), which is located in the main body of the prosthesis. The electrical contact members 50*a*, 50*b* and the electrical contact surfaces 52*a*, 52*b* are arranged to slidably contact one another as the moveable component 12 rotates about the worm gear wheel 18. In this arrangement the electrical contact members 50*a*, 50*b* slide along the electrical contact surfaces 52*a*, 52*b* maintaining an electrical contact between the electrical contact members 50*a*, 50*b* and the electrical contact surfaces 52*a*, 52*b* as the moveable component 12 rotates about the worm gear wheel 18.

The electrical contact members 50*a*, 50*b* are metal pin members. The electrical contact members 50*a*, 50*b* are housed in first housing (grip housing) 54*a*. As best illustrated in FIGS. 3 and 5, the first housing 54*a* and a second housing (grip housing) 54*b* (to be described below) are located within the proximal housing 30*a*, or, more specifically, within the lugs 26. The electrical contact members 50*a*, 50*b* are arranged such that they are biased towards the electrical contact surfaces 52*a*, 52*b*. The electrical contact members 50*a*, 50*b* are spring biased towards the electrical contact surfaces 52*a*, 52*b*. A spring (not illustrated) is arranged between the first housing 54*a* and the electrical contact members 50*a*, 50*b*. The spring biases the electrical contact members 50*a*, 50*b* towards the electrical contact surfaces 52*a*, 52*b*. Each electrical contact member 50*a*, 50*b* may be biased by a separate spring.

The pin members are arranged to have substantially flat head portions (not illustrated). It is the head portions which make contact with the electrical contact surfaces 52*a*, 52*b*. The head portions may include a chamfered, or curved edge portion. Alternatively, the head portion may be substantially dome-shaped.

As an alternative to pin members, the electrical contact members may comprise, for example, brushes or sprung contacts.

As best illustrated in FIGS. 4 to 8, the electrical contact surfaces 52*a*, 52*b* are arc-shaped elongate metal tracks. The shape and length of the electrical contact surfaces 52*a*, 52*b* are arranged to follow the path of the moveable component 12 (and the electrical contact members 50*a*, 50*b*) as it rotates about the worm gear wheel 18.

The electrical contact surfaces 52*a*, 52*b* are provided on support member 58 and the support member 58 is fixed to the worm gear wheel 18, with, for example, an adhesive. The support member 58 may be flexible, rigid or at least partially flexible or rigid. The support member 58 may be a flexible sheet, a rigid sheet, or an at least partially flexible or rigid sheet. Alternatively, the electrical contact surfaces 52*a*, 52*b* are etched onto the worm gear wheel 18.

Figure 7:
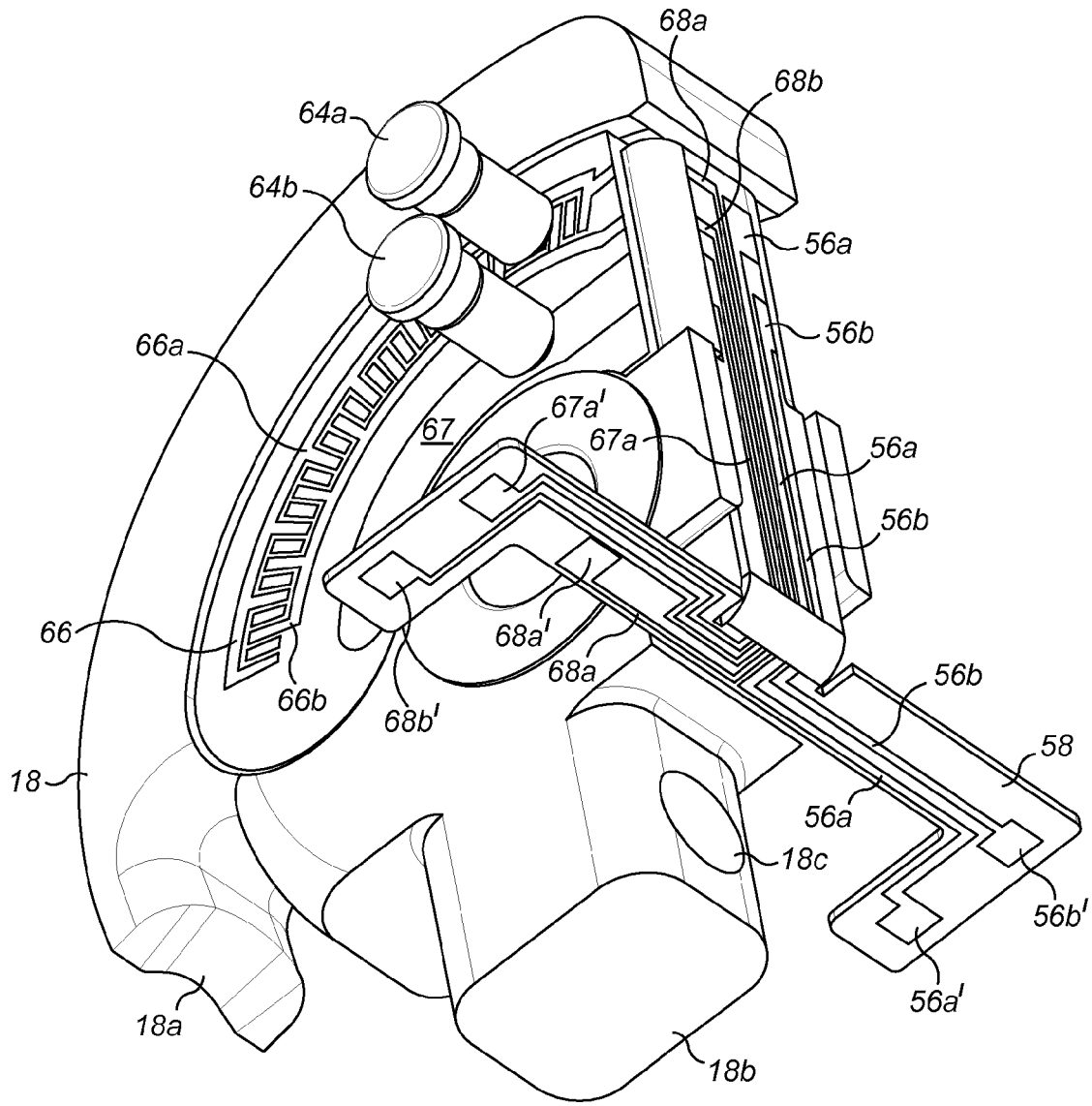
FIG. 7 is perspective view of the worm gear wheel of FIG. 6.
Figure 8:
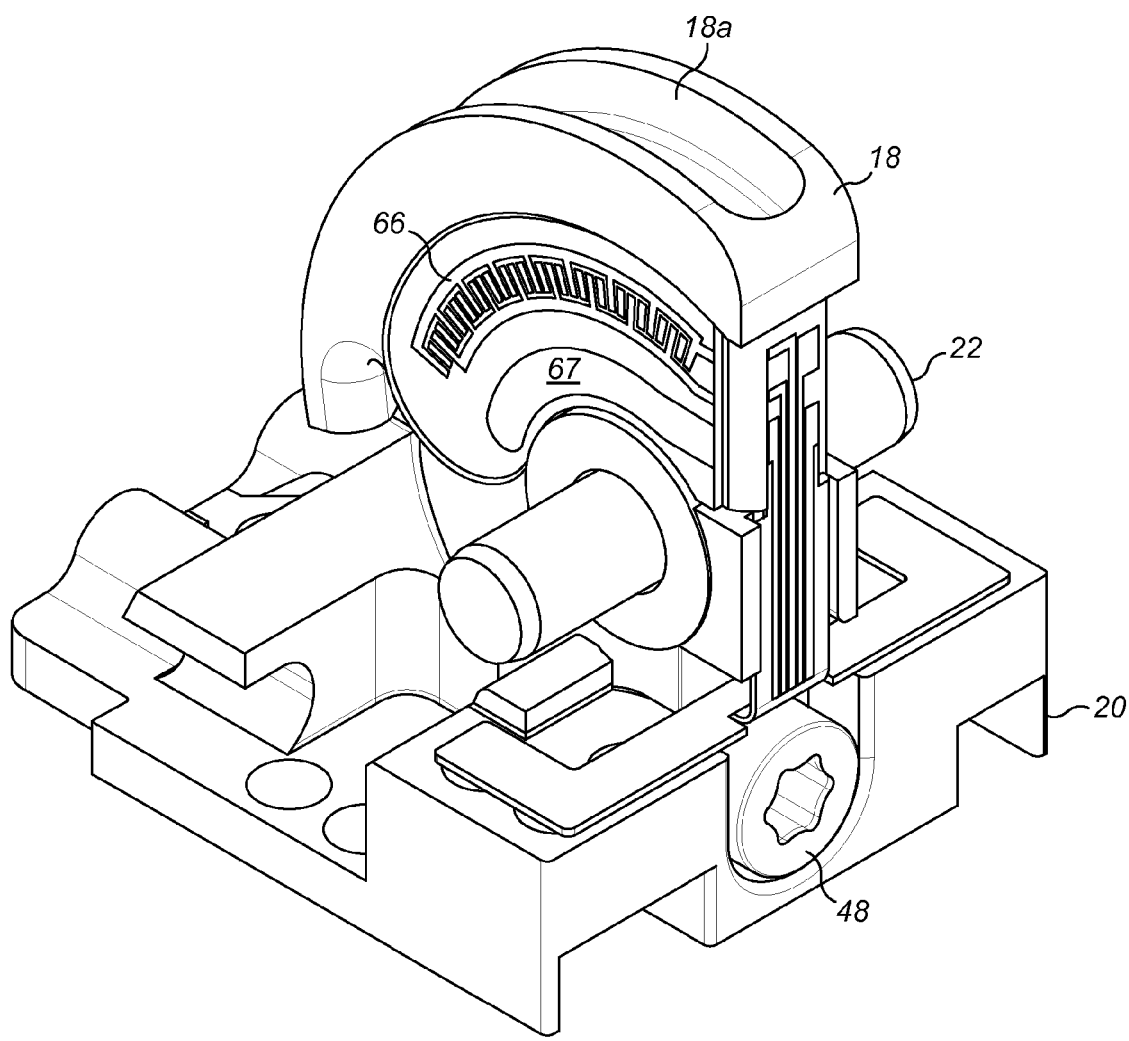
FIG. 8 is a perspective view of the worm gear wheel of FIG. 6 mounted to a support member of the hand prosthesis.

As best illustrated in FIG. 7, the electrical contact surfaces 52*a*, 52*b* include two electrical connections 56*a*, 56*b*. The electrical connections 56*a*, 56*b* are used to provide power to the motor 14. The electrical connections 56*a*, 56*b* are provided on the support member 58 and the support member 58 is fixed to the worm gear wheel 18, with, for example, an adhesive. Alternatively the electrical connections 56*a*, 56*b* may be etched onto the worm gear wheel 18.

The electrical connections 56*a*, 56*b* include two electrical contact points 56*a*', 56*b*' for connecting the electrical connections 56*a*, 56*b* to the electrical power source. Part of the electrical connections 56*a*, 56*b* and the electrical contact points 56*a*', 56*b*' are provided on the support member 58.

Figure 9:
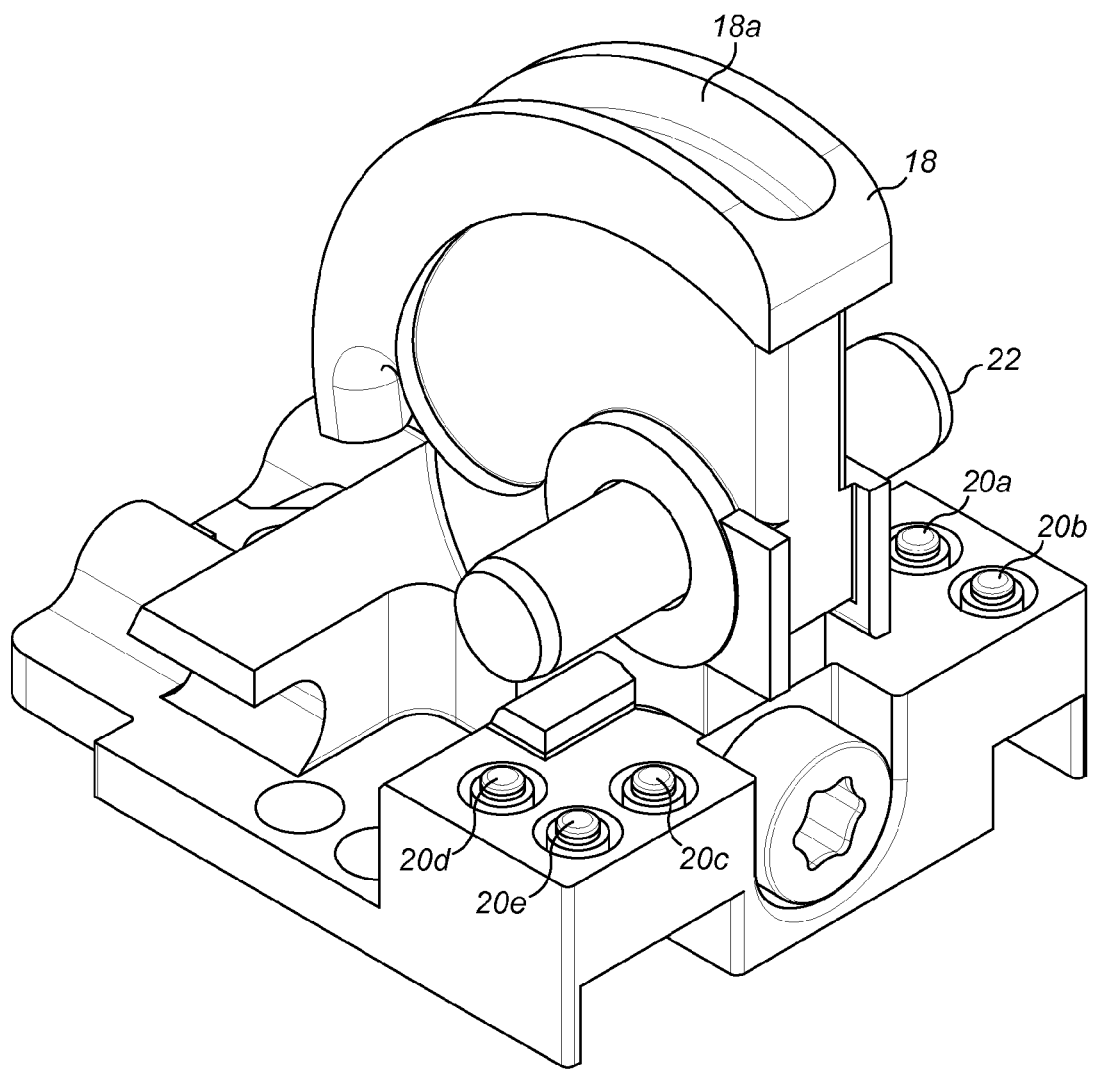
FIG. 9 is a perspective view of the worm gear wheel and support member of FIG. 7 with the at least one electrical contact surface removed.

As illustrated in FIG. 9, the support member 20 includes two electrical connection points 20*a*, 20*b*. The electrical contact points 56*a*', 56*b*' are arranged such that they contact the electrical connection points 20*a*, 20*b* of the support member 20 when the support member 58 (and electrical contact surfaces 52*a*, 52*b*) is fitted to the worm gear wheel 18 and connected to the support member 20.

The electrical connection points 20*a*, 20*b* are connected to the electrical power source via electrical wires (not illustrated).

As described above, the electrical contact members 50*a*, 50*b* and the electrical contact surfaces 52*a*, 52*b* are used to supply electrical power to the motor 14. The electrical contact surfaces 52*a*, 52*b* may provide AC or DC electrical power to the motor 14 via the electrical contact members 50*a*, 50*b*. In the present embodiment the hand prosthesis 10 a variable electrical power source (not illustrated) which provides DC electrical power to the motor 14. The power source is connected to the electrical connection points 20*a*, 20*b* of the support member 20. Electrical power is transferred from the electrical connection points 20*a*, 20*b* to the motor 14 via the electrical connections 56*a*, 56*b*, the electrical contact surfaces 52*a*, 52*b* and the electrical contact members 50*a*, 50*b*. The electrical contact surfaces 52*a*, 52*b* are arranged to be supplied with electrical power at between 0V and 12V.

As illustrated in FIGS. 5 to 8, the hand prosthesis 10 also includes a position sensing device 60 for sensing the position of the moveable component 12 relative to the worm gear wheel 18. The position sensing device 60 includes an encoder 62, where the encoder 62 is operable to produce an output signal which is indicative of the position of the moveable component 12 relative to the worm gear wheel 18.

The encoder 62 includes two electrical contact members 64*a* and 64*b* and two electrical contact surfaces 66 and 67. The electrical contact members 64*a*, 64*b* are metal pin members and are housed in the second housing 54*b*. The electrical contact members 64*a*, 64*b* have the same substantially flat head as the electrical contact members 50a, 50b. The electrical contact members 64a, 64b are also spring biased towards the electrical contact surfaces 66, 68 in the same manner as the electrical contact members 50a, 50b.

The two electrical contact members 64a, 64b are electrically connected via an electrical wire (not illustrated). The electrical wire may be soldered (or otherwise fixed) to each contact member 64a, 64b.

The electrical contact surfaces 66, 67 are positioned on the worm gear wheel 18. The electrical contact surfaces 66, 67 are arc-shaped elongate metal tracks. The shape and length of the electrical contact surfaces 66, 67 are arranged to follow the path of the moveable component 12 (and the electrical contact members 64a, 64b) as it rotates about the worm gear wheel 18. The electrical contact surfaces 66, 67 are provided on the support member 58 (with the electrical contact surfaces 52a, 52b). Alternatively, the electrical contact surfaces 66, 67 may be etched onto the worm gear 18.

The electrical contact members 64a 64b and the electrical contact surfaces 66, 67 are arranged such that a sliding contact is maintained between the electrical contact members 64a, 64b and the electrical contact surfaces 66, 67 as the moveable component 12 rotates about the worm gear wheel 18.

As illustrated best in FIGS. 5 to 8 and 10, the electrical contact surface 66 includes a first electrical contact surface 66a and a second electrical contact surface 66b. The first and second electrical contact surfaces 66a, 66b are electrically isolated from one another. The first and second electrical contact surfaces 66a, 66b are arranged such that they at least partially overlap in the direction of the path of the electrical contact member 64a is it rotates about the worm gear wheel 18. The partially overlapping areas of the first and second electrical contact surfaces 66a, 66b have equally sized spacings, or gaps, therebetween. This is termed the main operational area, or portion, of the first and second electrical contact surfaces 66a, 66b.

The first and second electrical contact surfaces 66a, 66b are arranged such that the electrical contact member 64a alternately electrically connects and disconnects the first electrical contact surface 66a and the second electrical contact surface 66b as it rotates about the worm gear wheel 18. The electrical contact surface 66 also includes bridge components 65 which are located between the gaps of the first and second electrical contact surfaces 66a, 66b. The bridge components 65 are electrically neutral and are used to provide support to the electrical contact member 64a as it slides across the electrical contact surfaces 66a, 66b.

The electrical contact member 64a of the position sensing device 60 is arranged to always be in electrical contact with at least one of the first contact surface 66a and the second contact surface 66b of the position sensing device 60. However, it should be appreciated that the electrical contact member 64a of the position sensing device 60 may not necessarily always be in electrical contact with at least one of the first contact surface 66a and the second contact surface 66b of the position sensing device 60. For example, the electrical contact member 64a of the position sensing device 60 may not necessarily have to be in electrical contact with the first contact surface 66a and the second contact surface 66b of the position sensing device 60 as the moveable component 12 rotates about the worm gear wheel 18. It is possible that the electrical contact member 64 may be in physical contact with the worm gear wheel 18 and not necessarily make an electrical contact with first contact surface 66a and the second contact surface 66b of the position sensing device 60. A preferred arrangement is that, as the moveable component 12 rotates about the worm gear wheel 18, the electrical contact member 64a goes from being in contact with both first and second electrical contact surfaces 66a, 66b and a bridge component 65 (electrically connected) to being in contact with one of the first and second electrical contact surfaces 66a, 66b and two bridge components 65 (electrically disconnected).

Figure 10:
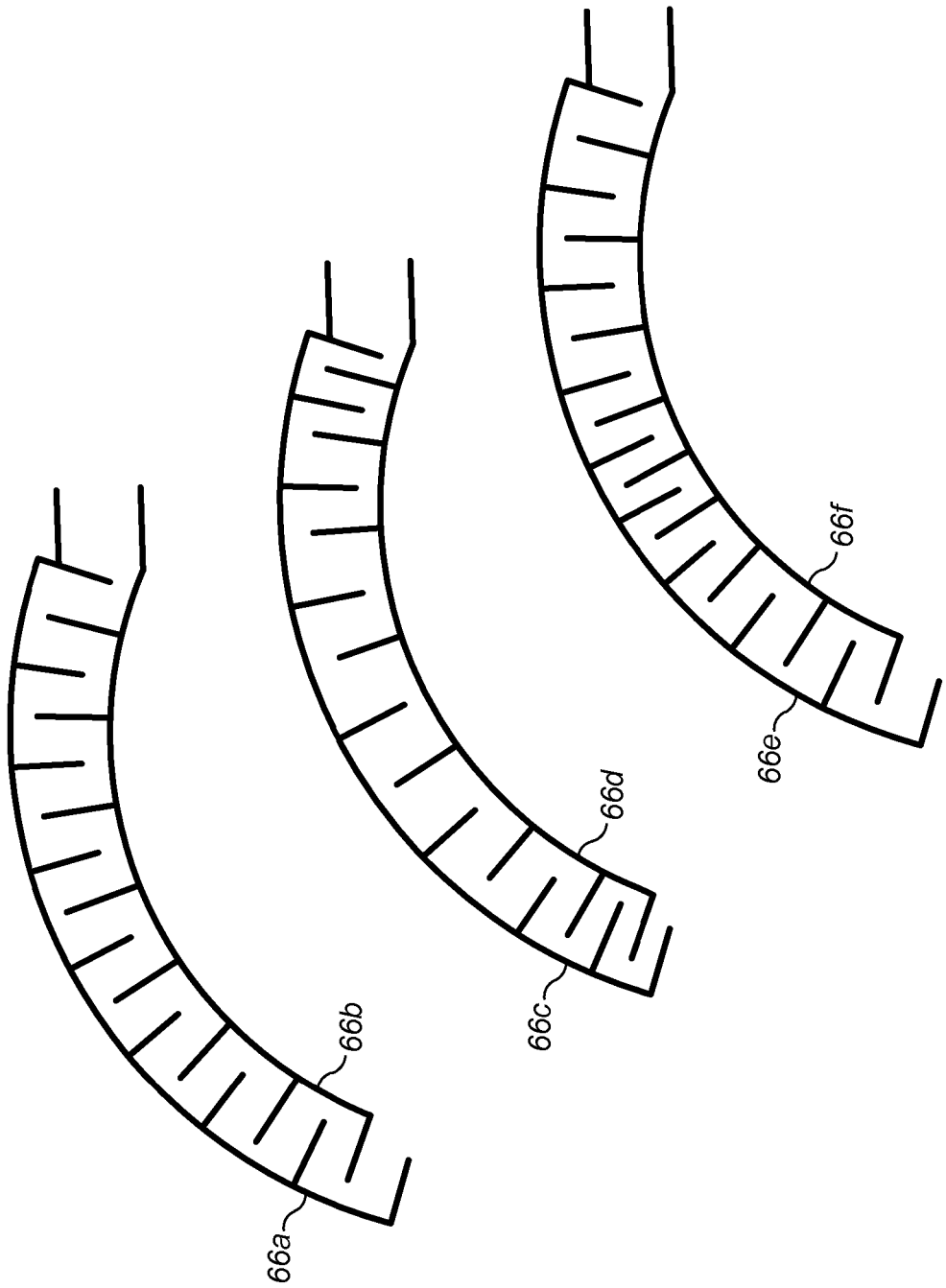
FIG. 10 illustrates different configurations of the partially overlapping areas of first and second electrical contact surfaces of the encoder.

As illustrated schematically in FIG. 10, the partially overlapping areas of the first and second electrical contact surfaces may also have a smaller operational area, or portion, where the spacings, or gaps, therebetween are less than, or greater than those in the main operational area, or portion. The smaller area may additionally, or alternatively, include spacings, or gaps, which reduce gradually, or increase gradually, in width in the direction of the path of the moveable component 12. With reference to FIG. 10, the partially overlapping areas of the first and second electrical contact surfaces 66c, 66d may have variable pitch along the direction of the path of the electrical contact member 64a as it rotates about the worm gear wheel 18. Such variable pitch may provide for a more fine pitch at either or both ends of the path. Electrical contact surfaces 66c, 66d in this example have a fine pitch at both ends of the path. The electronic device, which is configured to control the operation of the motor, will respond to the fine pitch by slowing down the motor speed at either or both extremes. This may prevent motor overload at either or both extremes of movement of the digit. Such variable pitch may also or alternatively provide for a more fine pitch at another region of the path, such as the centre of the path, as illustrated in FIG. 10 by first and second electrical contact surfaces 66e and 66f. The electronic device, which is configured to control the operation of the motor, will respond to the fine pitch by slowing down the movement in the region. This may allow a precision pinch movement by the user of the prosthesis or orthosis. The bridge components may be used in the arrangements with example shown in FIG. 10, but for simplicity in FIG. 10, the bridge components are not shown.

As best illustrated in FIG. 7, the first and second electrical contact surfaces 66a, 66b include first and second electrical connections 68a, 68b. As described above, the electrical contact surfaces 66a, 66b are provided on the support member 58. Alternatively, the electrical contact surfaces 66a, 66b may be etched onto the worm gear 18.

The electrical contact surface 67 is used to supply electrical power to the position sensing device 60 and encoder 62. The electrical contact surface 67 is connected to an electrical power source (not illustrated). The electrical power source may be the same power source as described above, or may be an additional electrical power source.

The first and second electrical connections 68a, 68b include two electrical contact points 68a', 68b' for outputting an electrical signal from the first and second electrical contact surfaces 66a, 66b. Part of the first and second electrical connections 68a, 68b and the electrical contact points 68a', 68b' are provided on the support member 58.

The electrical contact surface 67 includes an electrical connection 67a. The electrical connection includes an electrical contact point 67a' for connecting the electrical contact surface 67 to the electrical power source.

As illustrated in FIG. 9, the support member 20 further includes three electrical connection points 20c and 20d and 20e. The electrical contact points 68a', 68b', 67a' are arranged such that they contact the electrical connection points 20c, 20d, 20e of the support member 20 when the support member 58 (and first and second electrical connections 68a, 68b, 67a) is fitted thereto.

The electrical connection point 20e is connected to the electrical power source via electrical wires (not illustrated).

As described above, the encoder 62 (electrical contact members 64a, 64b and the electrical contact surfaces 66, 67) is used to produce an output signal which is indicative of the position of the moveable component 12 relative to the worm gear wheel 18. The electrical contact surface 67 is connected to the electrical power source via the electrical connection 67a, the electrical contact point 67a' and the electrical connection point 20e. The electrical contact surface 67 is therefore held at between 0V and 12V. Since the electrical contact member 64b is in electrical contact with the electrical contact surface 67 and is electrically connected to the electrical contact member 64a, via the electrical wire, the electrical contact member 64a is also held at between 0V and 12V.

In this arrangement, since the first and second electrical contact surfaces 66a, 66b are electrically isolated from one another, but are at least partially overlapping the electrical contact member 64a is capable of completing the electrical circuit between the first and second electrical contact surfaces 66a, 66b when it contacts both the first and second electrical contact surfaces 66a, 66b as it rotates about the worm gear wheel 18. The electrical circuit is broken when the electrical contact member 64a does not contact both the first and second electrical contact surfaces 66a, 66b. In this arrangement the encoder 62 of the position sensing device 60 outputs an encoded signal in the form of a series of spaced apart voltage pulses (e.g. 0V to 12V) which can be decoded to indicate the position of the moveable component 12 relative to the worm gear wheel 18. The encoded signal is output from the first and second electrical contact surfaces 66a, 66b to the electrical connection points 20c, 20d, via the electrical connections 68a, 68b and the electrical contact points 68a', 68b'. That is, the series of spaced apart voltage pulses are read out from the encoder at electrical connection points 20c and 20d of the support member 20.

If the electrical contact member 64a of the position sensing device 60 enters the smaller operational area of the first and second electrical contact surfaces 66a, 66b where the spacings, or gaps, therebetween are changing or have changed (as described above), the output voltage pulses will differ from those produced in the larger operational area of the first and second electrical contact surfaces 66a, 66b. This signal can be used to indicate to the wearer of the hand prosthesis 10 that the moveable component 12 has been moved to an undesired position. For example, if an excessive load is placed on the moveable component 12. In this arrangement the hand prosthesis 10 includes an indicator device (not illustrated) which is arranged to output a signal to the wearer of the hand prosthesis 10 if the moveable component 12 has been moved to an undesired position. The output signal is in the form of an alert to the wearer. The alert may be a audible signal, a vibrational signal, or the like. The above components may be termed an "overload detection" device. The alert to the user may also occur where, due to the floating arrangement (play) of the worm gear 16, if the a signal is output from the electrical connection points 20c and 20d of the support member 20, i.e. the digit has moved, but this movement has not been instructed (see below). This lets the user know that unrequested movement of the digit is taking place.

The hand prosthesis 10 further comprises an electronic device (not illustrated) which is configured to control the operation of the motor 14 and the position sensing device 60. The electronic device is also configured to decode the output signal from the encoder 62 to determine the position of the moveable component 12 relative to the worm gear wheel 18 at any given time. The electronic device may be located within the main body of the prosthesis. The electronic device may also be configured to operate the alert to the user, as described above.

The motor 14 is operable via one or more switches (not illustrated). The switches may be actuated by residual movement of the wearer of the hand prosthesis 10, wrist and/or shoulder movement of the wearer of the hand prosthesis 10, or the like. Alternatively, or additionally, the motor 14 may be operable via signals derived from the activity of, or from, electromyographic (EMG) activity of residual muscle actions of the wearer of the hand prosthesis 10, pressure sensitive resistors on the wearer of the hand prosthesis 10, signals derived from one or more neural implants in the wearer of the hand prosthesis 10, EMG activity from reinnervated muscles, muscles of the feet and/or chest, or the like. The electronic device is configured to process the actuation signals from the wearer to operate the motor 14.

In use the wearer of the hand prosthesis 10 provides a movement signal, for example, an EMG signal, to operate the motor 14. When the motor 14 receives the signal, via the electronic device, the drive shaft 14b is operated (turned) in a chosen direction. This causes the worm gear 16 to rotate and rotate the moveable component 12 about the worm gear wheel 18. Depending on the EMG signal and hence the direction of operation of the drive shaft 14b, the moveable component 12 rotates about the worm gear wheel 18 with the first digit member 12a and second digit member 12b closing in a hand grasping action, or the first digit member 12a and second digit member 12b opening in a hand extension action.

Providing a hand prosthesis 10 having a moveable component 12 with at least one electrical contact member 50a, 50b and a worm gear wheel 18 with at least one electrical contact surface 52a, 52b, the at least one electrical contact member 50a, 50b and the at least one electrical contact surface 52a, 52b being arranged to slidably contact one another as the moveable component 12 rotates about the worm gear wheel 18, avoids the use of electrical power wires between moving components (worm gear wheel 18 and moveable component 12). In the arrangement of the present invention there is no movement of any electrical wires between the electrical contact surfaces 52a, 52b, the electrical contact members 50a, 50b and the motor 14. As a result of this, since there are no electrical wires, which eventually fail due to fatigue as a result of the large number of open and close cycles which the moveable component 12 goes through, the hand prosthesis 10 of the present invention can operate for far greater periods of time without failing, or requiring servicing.

Providing a position sensing device 60 (encoder 62) on the worm gear wheel 18 (or moveable component 12, see below) avoids the use of using a separate commercially available encoder, such as a motor encoder, which typically extends the size (length) of the motor. This means that the hand prosthesis 10 of the present invention can be reduced in size.

Modifications and improvements may be made to the above without departing from the scope of the present invention. For example, although the moveable component has been illustrated and described above as being a digit of a hand prosthesis, it should be appreciated that the moveable component may also be a thumb member of a hand prosthesis.

Furthermore, although the moveable component has been illustrated and described above as having a first digit member 12a and a second digit member 12b, it should be appreciated that the moveable component may comprise a third digit member. The third digit member may be pivotably connected to the second digit member. The second digit member may be coupled at its distal end to the third digit member to form a distal joint for allowing movement of the third digit member in relation to the second digit member. The second digit member may be coupled to the third digit member with a coupling mechanism.

Also, although the worm gear 16 has been illustrated and described above as being positioned within the moveable component 12, it should be appreciated that the worm gear 16 may be positioned outside of the moveable component 12. That is the worm gear 16 may be positioned outside of the first digit member 12*a*.

Furthermore, although the worm gear 16 has been illustrated and described above as having an axis of rotation which is coincident and parallel to the axis of rotation of the drive shaft 14*b*, it should be appreciated that the rotational axis of the worm gear may be inclined relative to the rotational axis of the motor drive shaft. The rotational axis of the worm gear may be substantially perpendicular to the rotational axis of the motor drive shaft. In this arrangement the moveable component may further comprise one or more transmission components to couple movement of the motor drive shaft to the worm gear. The one or more transmission components may include a bevelled gear arrangement. The bevelled gear arrangement may comprise a first bevel gear and a second bevel gear. The first and second bevel gears engage with each other, the first bevel gear being configured to move in response to movement of the motor drive shaft and the second bevel gear being coupled to the worm gear. The first and second bevel gears may be arranged such that they transmit rotation of the motor drive shaft and worm gear through approximately ninety degrees.

Also, although the electrical contact members 50*a*, 50*b* and the electrical contact surfaces 52*a*, 52*b* have been illustrated and described above as being positioned on the moveable component 12 and the worm gear wheel 18, respectively, it should be appreciated that the electrical contact members 50*a*, 50*b* may be positioned on the worm gear wheel 18 and the electrical contact surfaces 52*a*, 52*b* may be positioned on the moveable component 12.

Furthermore, although the electrical contact members 64*a*, 64*b* of the position sensing device 60 and the electrical contact surfaces 66, 67 of the position sensing device 60 have been illustrated and described above as being located on the moveable component 12 and the worm gear wheel 18, respectively, it should be appreciated that the electrical contact members 64*a*,64*b* of the position sensing device 60 may be located on the worm gear wheel 18 and the electrical contact surfaces 66, 67 of the position sensing device 60 may be located on the moveable component 12.

Also, although the position sensing device 60 has been illustrated and described above as being an electrical encoder, it should be appreciated that the position sensing device 60 may alternatively include an optical encoder or a magnetic encoder.

In the case of an optical encoder the position sensing device may include at least one optical reading member and at last one optically readable surface. The least one optical reading member may be positioned on one of the moveable component and the worm gear wheel or the support member and the at least one optically readable surface may be positioned on the other of the moveable component and the worm gear wheel or the support member. The at least one optical reading member and the at least one optically readable surface being arranged such that the at least one optical reading member is capable of optically reading the surface of the at least one optically readable surface as the moveable component rotates about the worm gear wheel.

The at least one optical reading member of the position sensing device may be positioned on the moveable component and the at least one optically readable surface of the position sensing device may be positioned on the worm gear wheel or the support member. The at least one optical reading member of the position sensing device may be positioned on the first digit member of the moveable component and the at least one optically readable surface of the position sensing device may be positioned on the worm gear wheel or the support member.

The at least one optical reading member of the position sensing device may be positioned on the worm gear wheel or the support member and the at least one optically readable surface of the position sensing device may be positioned on the moveable component. The at least one optical reading member of the position sensing device may be positioned on the worm gear wheel or the support member and the at least one optically readable surface of the position sensing device may be positioned on the first digit member of the moveable component.

The at least one optical reading member of the position sensing device and the at least one optically readable surface of the position sensing device may be arranged such that, when the motor is operated in use of the prosthesis or orthosis, the at least one optical reading member is capable of optically reading the surface of the at least one optically readable surface as the moveable component rotates about the worm gear wheel. In this arrangement the at least one optical reading member of the position sensing passes over the at least one optically readable surface of the position sensing device as the moveable component rotates about the worm gear wheel.

The at least one optical reading member of the position sensing device may be housed in a housing. The housing may be positioned in the moveable component, the worm gear wheel or the support member.

The at least one optically readable surface of the position sensing device may be an elongate track. The at least one optically readable surface of the position sensing device may be in the shape of an arc. The at least one optically readable surface of the position sensing device may be arc-shaped. The shape and length of the at least one optically readable surface of the position sensing device is arranged to follow the path of the moveable component as it rotates about the worm gear wheel. The shape and length of the at least one optically readable surface of the position sensing device is arranged to follow the path of the at least one optical reading member of the position sensing device as it rotates about the worm gear wheel.

At least a part of the at least one optically readable surface of the position sensing device may be provided on a flexible sheet. The flexible sheet may be positioned on the moveable component, the worm gear wheel or the support member. The flexible sheet may be fixedly attached to the moveable component, the worm gear wheel or the support member. The flexible sheet may be fixedly attached to the moveable component, the worm gear wheel or the support member with one or more adhesives.

The at least one optically readable surface of the position sensing device may include one or more electrical connections for operation of the position sensing device. The at least one optically readable surface of the position sensing device may include one or more electrical power connections for operation of the position sensing device. The one or more electrical connections of the at least one optically readable surface of the position sensing device may be arranged to connect with the one or more electrical connections of the support member.

The at least one optically readable surface of the position sensing device may comprise one or more optically readable patterns.

The at least one optically readable surface of the position sensing device may be arranged such that an alternate light/dark signal is read by the at least one optical reading member as the at least one optical reading member rotates about the worm gear wheel.

The at least one optical reading member may include a photocell. The at least one optically readable surface and the at least one optical reading member may include a photoemitter-detector pair.

The at least one optically readable surface may include an area where the optically readable pattern differs from a reference area.

The position sensing device outputs an encoded signal in the form of a series of spaced apart pulses. The output signal is indicative of the position of the moveable component relative to the worm gear wheel.

The position sensing device may further comprise an indicator device which may be arranged to output a signal to the user of the prosthesis or orthosis if the position of the moveable component relative to the worm gear wheel or the support member moves to an undesired position.

The indicator device may output the signal to the user when the at least one optical reading member of the position sensing device enters the area where the optical pattern of the optically readable surface differs from a reference optical pattern.

In the case of a magnetic encoder, the position sensing device may include at least one magnetic reading member and at last one magnetically readable surface. The least one magnetic reading member may be positioned on one of the moveable component and the worm gear wheel or the support member and the at least one magnetically readable surface may be positioned on the other of the moveable component and the worm gear wheel or the support member. The at least one magnetic reading member and the at least one magnetically readable surface being arranged such that the at least one magnetic reading member is capable of magnetically reading the surface of the at least one magnetically readable surface as the moveable component rotates about the worm gear wheel.

The at least one magnetic reading member of the position sensing device may be positioned on the moveable component and the at least one magnetically readable surface of the position sensing device may be positioned on the worm gear wheel or the support member. The at least one magnetic reading member of the position sensing device may be positioned on the first digit member of the moveable component and the at least one magnetically readable surface of the position sensing device may be positioned on the worm gear wheel or the support member.

The at least one magnetic reading member of the position sensing device may be positioned on the worm gear wheel or the support member and the at least one magnetically readable surface of the position sensing device may be positioned on the moveable component. The at least one magnetic reading member of the position sensing device may be positioned on the worm gear wheel or the support member and the at least one magnetically readable surface of the position sensing device may be positioned on the first digit member of the moveable component.

The at least one magnetic reading member of the position sensing device and the at least one magnetically readable surface of the position sensing device may be arranged such that, when the motor is operated in use of the prosthesis or orthosis, the at least one magnetic reading member is capable of magnetically reading the surface of the at least one magnetically readable surface as the moveable component rotates about the worm gear wheel. In this arrangement the at least one magnetic reading member of the position sensing passes over the at least one magnetically readable surface of the position sensing device as the moveable component rotates about the worm gear wheel.

The at least one magnetic reading member of the position sensing device may be housed in a housing. The housing may be positioned in the moveable component, the worm gear wheel or the support member.

The at least one magnetically readable surface of the position sensing device may be an elongate track. The at least one magnetically readable surface of the position sensing device may be in the shape of an arc. The at least one magnetically readable surface of the position sensing device may be arc-shaped. The shape and length of the at least one magnetically readable surface of the position sensing device is arranged to follow the path of the moveable component as it rotates about the worm gear wheel. The shape and length of the at least one magnetically readable surface of the position sensing device is arranged to follow the path of the at least one magnetic reading member of the position sensing device as it rotates about the worm gear wheel.

At least a part of the at least one magnetically readable surface of the position sensing device may be provided on a flexible sheet. The flexible sheet may be positioned on the moveable component, the worm gear wheel or the support member. The flexible sheet may be fixedly attached to the moveable component, the worm gear wheel or the support member. The flexible sheet may be fixedly attached to the moveable component, the worm gear wheel or the support member with one or more adhesives.

The at least one magnetically readable surface of the position sensing device may include one or more electrical connections for operation of the position sensing device. The at least one magnetically readable surface of the position sensing device may include one or more electrical power connections for operation of the position sensing device. The one or more electrical connections of the at least one magnetically readable surface of the position sensing device may be arranged to connect with the one or more electrical connections of the support member.

The at least one optically readable surface of the position sensing device may comprise one or more optically readable patterns.

The at least one magnetically readable surface of the position sensing device may be arranged such that an alternating magnetic field is read by the at least one magnetic reading member as the at least one magnetic reading member rotates about the worm gear wheel. The at least one magnetically readable surface of the position sensing device may be arranged such that changes in a magnetic field is read by the at least one magnetic reading member as the at least one magnetic reading member rotates about the worm gear wheel.

The at least one magnetic reading member may include a permanent magnet. The at least one magnetically readable surface and the at least one magnetic reading member may include a ferrous metal and a magnetic pick-up that contains a permanent magnet.

The at least one magnetically readable surface may include an area where the magnetically readable pattern differs from a reference area.

The position sensing device outputs an encoded signal in the form of a series of spaced apart pulses. The output signal is indicative of the position of the moveable component relative to the worm gear wheel.

The position sensing device may further comprise an indicator device which may be arranged to output a signal to the user of the prosthesis or orthosis if the position of the moveable component relative to the worm gear wheel or the support member moves to an undesired position.

The indicator device may output the signal to the user when the at least one magnetic reading member of the position sensing device enters the area where the magnetic pattern of the magnetically readable surface differs from a reference magnetic pattern.

Furthermore, although the hand prosthesis 10 of the present invention has been illustrated and described above as including a single moveable component 12, it should be appreciated that the hand prosthesis 10 may include two or more moveable components. The prosthesis or orthosis may comprise a plurality of moveable components and worm gear wheels. Each moveable component having a motor operable to drive a worm gear and each worm gear wheel fixedly mounted on a support member. The moveable components each extending generally tangentially with respect to their respective worm gear wheel and each being mounted for rotation about their respective worm gear wheel, each worm gear being in engagement with the respective worm gear wheel such that, when the motor is operated in use, the moveable component rotates about the worm gear wheel, wherein for each moveable component and worm gear wheel pair one of the moveable component and the worm gear wheel or the support member includes at least one electrical contact member and the other of the moveable component and the worm gear wheel or the support member includes at least one electrical contact surface, the at least one electrical contact member and the at least one electrical contact surface being arranged to slidably contact one another as the moveable component rotates about the worm gear wheel.

Also, although the first and second electrical contact surfaces 66a, 66b of the position sensing device 60 have been illustrated and described above as having overlapping tracks, with lateral interwoven finger portions, it should be appreciated that the first and second electrical contact surfaces 66a, 66b may have any suitable overlapping pattern which allows alternate electrical connection and disconnection therebetween as the electrical contact member 64a slides across the two surfaces. Also, it should be appreciated that any suitable change in pattern of the first and second electrical contact surfaces 66a, 66b may be used to operate as an overload indicator device.

Furthermore, it should be appreciated that the power supply to the motor 14 and the position sensing device 60 could be variable at any suitable voltage between 0V and 12V, or greater than 12V, if required.

The invention claimed is:

1. A prosthesis comprising:
   a moveable component having a motor operable to drive a worm gear;
   a worm gear wheel fixedly mounted on a support member of the prosthesis; and
   a position sensing encoder for sensing the position of the moveable component relative to the worm gear wheel or the support member, the position sensing encoder including at least one electrical contact member and first and second electrical contact surfaces, each electrical contact surface comprising a plurality of electrical contact elements;
   wherein the moveable component extends generally tangentially with respect to the worm gear wheel and is mounted for rotation about the worm gear wheel, the worm gear being in engagement with the worm gear wheel such that, when the motor is operated in use of the prosthesis, the moveable component rotates about the worm gear wheel,
   wherein one of the moveable component and the worm gear wheel or the support member includes the at least one electrical contact member and the other of the moveable component and the worm gear wheel or the support member includes at least one of the first or second electrical contact surfaces, the at least one electrical contact member and at least one of the first or second electrical contact surfaces being arranged to slidably contact one another as the moveable component rotates about the worm gear wheel to thereby provide a plurality of output pulses indicative of the position of the movable component.

2. A prosthesis according to claim 1, wherein the at least one electrical contact member and at least one of the first or second electrical contact surfaces are arranged such that, when the motor is operated in use, an electrical contact is maintained between the at least one electrical contact member and at least one of the first or second electrical contact surfaces as the moveable component rotates about the worm gear wheel.

3. A prosthesis according to claim 1, wherein the at least one electrical contact member is biased towards at least one of the first or second electrical contact surfaces.

4. A prosthesis according to claim 1, wherein the at least one electrical contact member comprises a pin member, the pin member comprising a substantially flat head portion which is arranged to contact at least one of the first or second electrical contact surfaces, or a dome-shaped head portion which is arranged to contact at least one of the first or second electrical contact surfaces.

5. A prosthesis according to claim 1, wherein the at least one electrical contact member is housed in a housing which is positioned in the moveable component, the worm gear wheel or the support member.

6. A prosthesis according to claim 5, wherein the housing includes one or more biasing devices for biasing the at least one electrical contact member towards at least one of the first or second electrical contact surfaces.

7. A prosthesis according to claim 1, wherein at least one of the first or second electrical contact surfaces is an elongate track.

8. A prosthesis according to claim 1, wherein at least one of the first or second electrical contact surfaces is arc-shaped and the shape and length of at least one of the first or second electrical contact surfaces is arranged to follow a path of the at least one electrical contact member as it rotates about the worm gear wheel.

9. A prosthesis according to claim 1, wherein at least a part of at least one of the first or second electrical contact surfaces is etched onto the moveable component, the worm gear wheel or the support member.

10. A prosthesis according to claim 1, wherein at least a part of at least one of the first or second electrical contact surfaces is provided on a support member, the support member being a sheet which is fixedly attachable to the moveable component, the worm gear wheel or the support member.

11. A prosthesis according to claim 1, wherein at least one of the first or second electrical contact surfaces includes one or more electrical connections for operation of the motor.

12. A prosthesis according to claim 11, wherein the one or more electrical connections of at least one of the first or second electrical contact surfaces are arranged to connect with the one or more electrical connections of the support member.

13. A prosthesis according to claim 1, wherein the prosthesis includes two electrical contact members, a first electrical contact member being arranged to be in sliding contact with the first electrical contact surface and a second electrical contact member being arranged to be in sliding contact with the second electrical contact surface.

14. A prosthesis according to claim 1, wherein the position sensing encoder is operable to produce an output signal indicative of the position of the moveable component relative to the worm gear wheel or the support member.

15. A prosthesis according to claim 14, wherein the output signal is an encoded signal and the position sensing encoder further includes an encoder, the encoder being operable to produce an output signal indicative of the position of the moveable component relative to the worm gear wheel or the support member.

16. A prosthesis according to claim 1, wherein the least one electrical contact member is positioned on one of the moveable component and the worm gear wheel or the support member and at least one of the first or second electrical contact surfaces is positioned on the other of the moveable component and the worm gear wheel or the support member.

17. A prosthesis according to claim 1, wherein the at least one electrical contact member of the position sensing encoder comprises a pin member, the pin member comprising a substantially flat head portion which is arranged to contact at least one of the first or second electrical contact surfaces, or a dome-shaped head portion which is arranged to contact at least one of the first or second electrical contact surfaces.

18. A prosthesis according to claim 1, wherein at least one of the first or second electrical contact surfaces of the position sensing encoder is an elongate track.

19. A prosthesis according to claim 1,
wherein the first contact surface and the second contact surface of the position sensing encoder comprises at least partially overlapping elongate tracks, and
wherein the partially overlapping areas of the first and second elongate tracks additionally include an area where the spacing between the first and second tracks reduces or increases gradually.

20. A prosthesis according to claim 19, further comprising an indicator device arranged to output a signal to a user when the at least one electrical contact member of the position sensing encoder enters the area where the spacing between the first and second tracks reduces gradually or increases gradually, or where the spacing between the first and second tracks is less than or greater than a main operational area.

21. A prosthesis according to claim 1, wherein the position sensing encoder includes at least one optical reading member and at last one optically readable surface.

22. A prosthesis according to claim 21, wherein the at least one optical reading member includes a photocell or a photo-emitter-detector pair.

23. A prosthesis according to claim 21, wherein the position sensing encoder outputs an encoded signal in the form of a series of spaced apart pulses, the encoded signal being indicative of the position of the moveable component relative to the worm gear wheel.

24. A prosthesis according to claim 21, wherein the position sensing encoder further comprises an indicator device that outputs a signal to a user when the at least one optical reading member of the position sensing encoder enters the smaller operational area where an optical pattern of the optically readable surface differs from the main operational area.

25. A prosthesis according to claim wherein the position sensing encoder includes at least one magnetic reading member and at last one magnetically readable surface.

26. A prosthesis according to claim 25, wherein the at least one magnetic reading member includes a permanent magnet.

27. A prosthesis according to claim 25, wherein the at least one magnetically readable surface includes a main operational area where the magnetically readable surface does not change and a smaller operational area where the magnetically readable surface is different to that of the main operational area.

28. A prosthesis according to claim 27, wherein the indicator device outputs the signal to a user when the at least one magnetic reading member of the position sensing encoder enters the smaller operational area where the magnetic pattern of the magnetically readable surface differs from the main operational area.

29. A prosthesis according to claim 1, wherein the first and second contact surfaces are elongate tracks.

30. A prosthesis according to claim 29, wherein the first and second contact surfaces are arc-shaped and the shape and length of the first and second contact surfaces are arranged to follow a path of the at least one electrical contact member of the position sensing encoder as it rotates about the worm gear wheel.

31. A prosthesis according to claim 1, wherein the first contact surface and the second contact surface of the position sensing encoder are electrically isolated from one another.

32. A prosthesis according to claim 31, wherein the first contact surface and the second contact surface of the position sensing encoder are arranged such that the at least one electrical contact member of the position sensing encoder alternately electrically connects and electrically disconnects the first contact surface and the second contact surface as the at least one electrical contact member rotates about the worm gear wheel.

33. A prosthesis according to claim 31, wherein the first and second elongate tracks of the position sensing encoder at least partially overlap in the direction of a path of the at least one electrical contact member as it rotates about the worm gear wheel.

34. A prosthesis according to claim 33, wherein the partially overlapping areas of the first and second elongate tracks includes an area of equal spacing between the first and second tracks.

* * * * *